United States Patent [19]

Miller, Jr. et al.

[11] Patent Number: 5,141,131

[45] Date of Patent: Aug. 25, 1992

[54] METHOD AND APPARATUS FOR THE ACCELERATION OF A PROPELLABLE MATTER

[75] Inventors: Theodore E. Miller, Jr.; Bradley C. Schuchardt; Alan R. Gould, all of Midland, Mich.; Thomas A. Skokut, Champaign, Ill.

[73] Assignee: DowElanco, Indianapolis, Ind.

[21] Appl. No.: 636,031

[22] Filed: Dec. 28, 1990

Related U.S. Application Data

[63] Continuation-in-part of Ser. No. 477,688, Feb. 9, 1990, abandoned, which is a continuation-in-part of Ser. No. 374,406, Jun. 30, 1989, abandoned.

[51] Int. Cl.⁵ .............................................. B67D 5/00
[52] U.S. Cl. ........................................ 222/54; 222/108; 222/226; 222/399; 222/630; 239/413
[58] Field of Search ............. 222/54, 108, 136, 144.5, 222/146.2, 226, 399, 630; 239/75, 135, 121, 407, 413, 416.1, 417.5

[56] References Cited

U.S. PATENT DOCUMENTS

| | | | |
|---|---|---|---|
| 2,189,448 | 2/1940 | McCrory | 222/136 X |
| 2,932,128 | 4/1960 | Porter et al. | 47/58 |
| 3,069,809 | 12/1962 | Simmons | 47/57.5 |
| 3,193,148 | 7/1965 | Anthon | 222/108 |
| 3,708,121 | 1/1973 | Hall et al. | 239/99 |
| 4,055,279 | 10/1977 | Lapera et al. | 222/54 |
| 4,302,670 | 11/1981 | Zaderej | 250/324 |
| 4,335,836 | 6/1982 | Harvill | 222/108 |
| 4,487,333 | 2/1984 | Pounder et al. | 222/504 X |
| 4,763,079 | 8/1988 | Neil | 328/233 |
| 4,767,402 | 8/1988 | Kost et al. | 604/22 |
| 4,812,047 | 3/1989 | Baumann | 222/399 X |
| 4,849,355 | 7/1989 | Wong | 435/172.3 |
| 4,970,154 | 11/1990 | Chang | 435/172.2 |
| 5,013,660 | 5/1991 | Kasuya | 435/173 |
| 5,036,006 | 7/1991 | Sanford et al. | 435/170.1 |

FOREIGN PATENT DOCUMENTS

| | | |
|---|---|---|
| 6838990 | 12/1990 | Austria. |
| 270356 | 12/1987 | European Pat. Off. |
| 9100915 | 1/1991 | PCT Int'l Appl. |
| 9111526 | 8/1991 | PCT Int'l Appl. |

OTHER PUBLICATIONS

Klein et al. Transfer of Foreign Genes into Intact Maize Cells with High-velocity Microprojectiles (1988), *Proc. Natl. Acad Sci. USA*, 85:4305-4309.

Sanford J., The Biolistic Process (1988), *Elsevier Science Publishers Ltd.*

Klein, et al., Factors Influencing Gene Delivery into Zea Mays Cells by High-velocity Microprojectiles (1988), *Biotechnology*, 6:559-563.

Fraley, et al., Liposome-mediated Delivery of... Interactions (1982), *Proc. Natl. Acad. Sci. USA*, 79:1859-1863.

Fukunaga, et al., Liposome-mediated Infection of Plant Protoplasts with Tobacco Mosaic Virus RNA (1981), *Virology*, 113:752-760.

Steinbiss and Broughton (1983), Mechanisms of Gene Uptake in Protoplasts, *International Review of Cytology*, 16:191-208.

*Primary Examiner*—Kevin P. Shaver
*Assistant Examiner*—Joseph A. Kaufman
*Attorney, Agent, or Firm*—Thomas D. Zindrick; Kenneth L. Loertscher

[57] ABSTRACT

An apparatus and method are taught for the acceleration of a propellable matter at selected target matter.

14 Claims, 9 Drawing Sheets

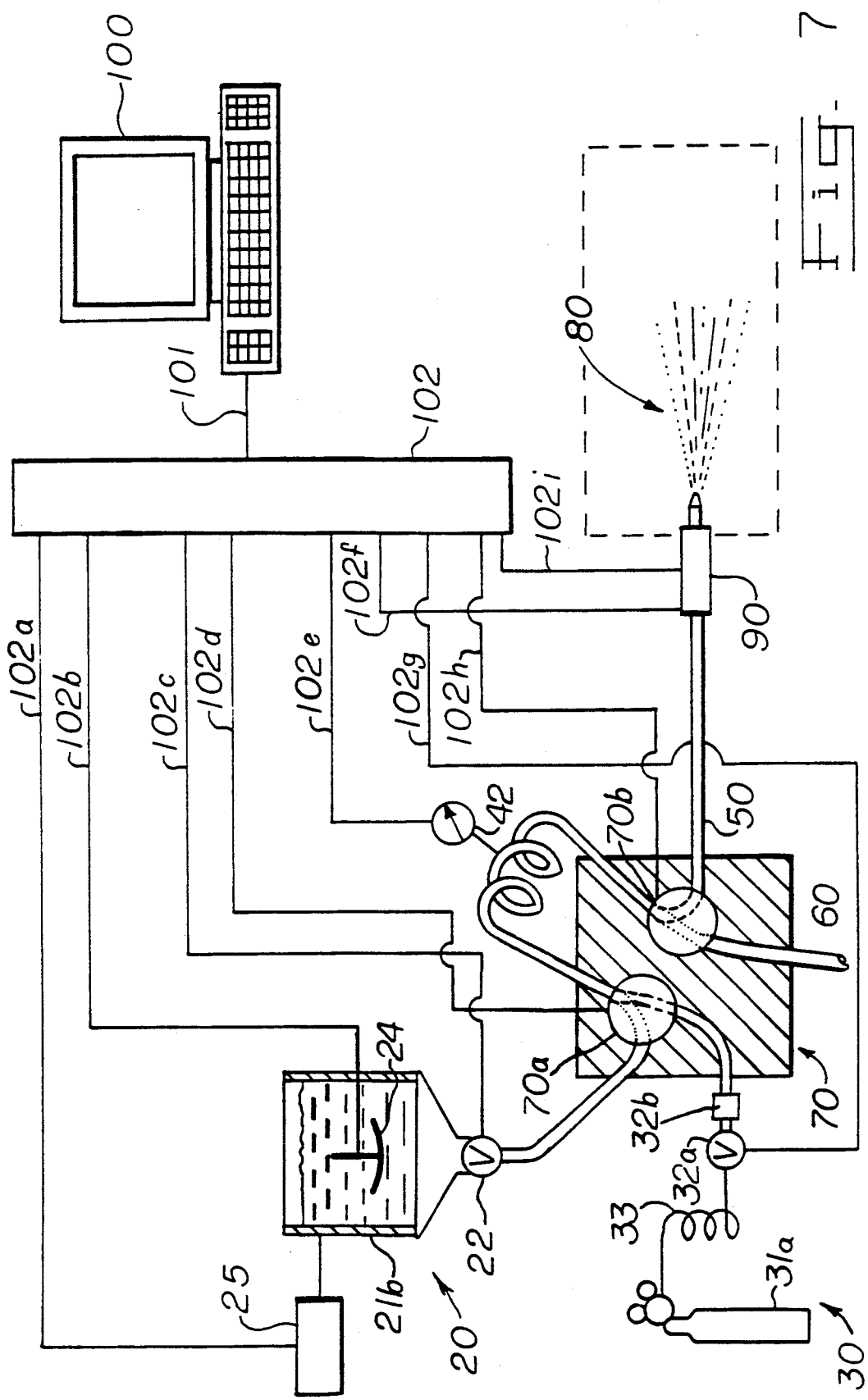

METHOD AND APPARATUS FOR THE ACCELERATION OF A PROPELLABLE MATTER

CROSS-REFERENCE TO RELATED APPLICATION

This application is a continuation-in-part of the co-pending application Ser. No. 477,688, filed Feb. 9, 1990 now abandoned; and a continuation-in-part of the co-pending application Ser. No. 374,406, filed Jun. 30, 1989, now abandoned.

FIELD OF THE INVENTION

The present invention is directed to an apparatus and method for the acceleration of propellable matter. More specifically, the present invention is directed to an apparatus and method for contacting a predetermined volume of gas under pressure with a predetermined volume of a suspension of propellable matter, and, thereafter, the suspension is accelerated at selected target matter.

BACKGROUND AND OBJECTS OF THE INVENTION

Biologists commonly wish to introduce a wide range of biological material into living cells. There exists much current research directed to the genetic transformation of living cells. Conventional technologies for introducing biological material into living cells includes electroporation, direct DNA uptake mechanisms, fusion mechanisms, microinjection mechanisms, and the use of infectious agents. However, each of these techniques suffer from some practical disadvantages.

Electroporation is a method for introducing a variety of molecules into cells by subjecting them to brief high-voltage electric pulses. For a general discussion of electroporation. see Electroporation of Eukaryotes and Prokaryotes: A General Approach to the Introduction of Macromolecules into Cells, 1988, K. Shigekawa and W. J. Dower, *Biotechniques*, 6:742; High-voltage Electroporation of Bacteria: Genetic Transformation of Campylobacter jejuni with Plasmid DNA, 1988, J. C. Miller, W. J. Dower, L. S. Tomkins, *Proc. Natl. Acad. Sci. USA*, 85:856-860; and A Simple and Rapid Method for Genetic Transformation of Lactic Streptococci by Electroporation, 1988, I. G. Powell, M. G. Achen, A. J. Hillier, B. E. Davidson, *Appl. Environ. Microbiol.*, 54:655-660.

General limitations of electroporation include (i) the reduction in overall cell viability caused by high applied voltages, and (ii) the inability to specifically target particular cells, especially in a complex multicellular organ.

Moreover, while electroporation methods have greatly increased the efficiency of uptake of chimeric gene constructions, such methods when used with plants are limited in plants to in vitro suspension systems. Moreover, although successfully used in the transformation of monocots as well as dicots (Expression of Genes Transferred into Monocot and Dicot Plant Cells by Electroporation, 1985, M. Fromm, L. P. Taylor, and V. Walbot, *Proc. Natl. Acad. Sci. USA*, 82:5824-5828). Electroporation methods generally require the relatively laborious and time-consuming step of removing the plant cell walls.

Uptake mechanisms generally involve suspensions of single cells, and specifically when applied to plant cells, require enzymatic removal of cell wall materials. Consequently, the uptake mechanisms are time consuming and have relatively low throughput.

One technique for uptake is the enhancement of membrane permeability by use of calcium (Ca) (Calcium Dependent Bacteriophage DNA Infection, 1972, M. Mandel and A. Higa. *J. Mol. Biol.*, 53:159-162); and temperature shock (Frozen-thawed Bacteria as Recipients of Isolated Coliphage DNA, 1972, S. Y. Dityatkin, K. V. Lisovskaya, N. N. Panzhava, B. N. Liashenk, *Biochimica et Biophysica Acta*, 281:319-323).

A second technique for uptake is the use of surface-binding agents such as polyethylene glycol (PEG). For a general discussion of surface-binding agent, see High Frequency Transformation of Bacillus subtilis Protoplasts by Plasmid DNA, 1972, S. Chang, and S. N. Cohen, *Mol. Gen. Genet.*, 168:111-115; In vitro Transformation of Plant Protoplasts With Ti-plasmid DNA, 1982, F. A. Krens, L. Molendijk, G. J. Wullems, and R. A. Schilperoort, *Nature*, 296:72); or such as calcium phosphate (A New Technique for the Assay of Infectivity of Human Adenovirus 5 DNA, 1973, F. L. Graham, and A. J. Van Der Eb, *Virology*, 52:456; Transformation of Mammalian Cells with Genes from Procaryotes and Eucaryotes, 1979, M. Wigler, R. Sweet, G. K. Sim, B. Wold, A. Pellicer, E. Lacy, T. Maniatis, S. Silverstein, and R. Axel, *Cell*, 16:777.

A third technique for uptake is the phagocytosis of particles into a cell. Suitable particles include liposomes (Liposome-mediated Transfer of Plasmid DNA into Plant Protoplasts, 1982, H. Uchimiya, T. Ohgawara, and H. Harada, In: A. Fujiwara (ed.), *Proc. 5th Intl. Cong. Plant Tissue and Cell Culture*, Jap. Assoc. for Plant Tissue Culture, Tokyo, pp. 507-508); organelles (Transplantation of Chloroplasts into Protoplasts of Petunia, 1973, I. Potrykus, *Z. Pflanzenphysiol.*, 70:364-366); or bacteria (Plant Cell Protoplasts Isolation and Development, 1972, E. C. Cocking, *Ann. Rev. Plant Physiol.*, 23:29-50).

Fusion mechanisms incorporate new genetic material into a cell by fusing a cell membrane with the membrane of another cell, an organelle, or a liposome. As with uptake mechanisms, plant cell fusion technologies rely upon the use of in vitro suspension systems, where cells are enzymatically stripped of any cell wall material.

Fusion can be induced with electric currents, PEG, and Sendai virus particles. For a general discussion of cell fusion, see Methods Using HVJ (Sendai Virus) for Introducing Substances into Mammalian Cells, 1980, T. Uchidaz, M. Yamaizumi, E. Mekada, Y. Okada, In: *Introduction of Macromolecules Into Viable Mammalian Cells*, C. Baserga, G. Crose, and G. Rovera (eds.) Wistar Symposium Series, Vol. 1, A. R. Liss, Inc., NY, pp. 169-185; and H. Harris, Cell Fusion: The Dunham Lectures, 1970, *Oxford University Press*.

While fusion technologies can have relatively good efficiencies in terms of numbers of cells affected, the problems of cell selection can be complex. For example, in the case of cell to cell fusion the resulting cells often have elevated ploidy, which can limit their usefulness.

Another technique is a direct method for the transfer of chromosomes by microinjection. Microinjection techniques employ extremely fine, drawn out capillary tubes which can be used as syringe needles for the direct injection of biological substances into certain types of individual cells. When small cells need to be injected, very sharp capillaries, whose tips are very easily broken or clogged, are required. Moreover, very high pressures are required to cause bulk flow through capillary apertures smaller than one micron and the regulation of such bulk flow can be difficult. The entire process is rather empirical, requiring different modifications for different cell types.

For a general discussion of microinjection techniques, see Methods for Microinjection Of Human Somatic Cells in Culture, 1973, E. G. Diacumakos, In: *Methods in Cell Biology*, D. M. Prescott (ed.), Academic Press, NY, pp. 287-311; Microinjection of Tissue Culture Cells, 1973, M. Graessman and A. Graessman, *Methods in Enzymology*, 101:482-492; Integration of Foreign DNA following Microinjection of Tobacco Mesophyll Protoplasts, 1986, A. Crossway, J. V. Oakes, J. M. Irvine, B. Ward, V. C. Knauf, C. K. Shewmaker, *Mol. Gen. Genet.*, 202:179-185; Micromanipulation Techniques in Plant Biotechnology, 1986, A. Crossway, H. Hauptli, C. M. Houck, J. M. Irvine, J. V. Oakes, L. A. Perani, *Biotechniques*, 4:320-334; A Detailed Procedure for the Intranuclear Microinjection of Plant Protoplasts, 1986, T. J. Reich, V. N. Iyer, B. Scobie, B. L. Miki, *Can. J. Bot.*; and Efficient Transformation of Alfalfa Protoplasts by the Intranuclear Microinjection of Ti Plasmids, 1986, T. J. Reich, V. N. Iyer, B. L. Miki, *Bio/Technology*, 4:1001-1004.

Microinjection techniques suffer from limitations in cell recovery. Direct microinjection of plant cells is further complicated by the presence of a rigid cell wall. While protoplasts lacking the cell wall can be formed, the microinjection of plant cell protoplasts is made difficult by their extreme fragility.

Thus, a disadvantage of microinjection is that it requires single cell manipulations and is, therefore, inappropriate for treating masses of cells. The process is generally very tedious and difficult. Consequently, it tends to have very low efficiency and low throughput.

In addition to the systems mentioned above, there exist several infectious agents which can deliver nucleic acids into cells. The plant pathogen Agrobacterium tumefaciens has the innate ability to transfer a portion of DNA from a Ti (Tumor-inducing) plasmid harbored therein into an infected plant cell. By inserting foreign genes into plasmids in Agrobacterium which carry certain sequences from the Ti plasmid, the bacterial transformational trait can be used to transport the foreign genes into the genome of the infected plant cells.

Of primary importance are the Agrobacterium vectors for dicot plant cells (Genetic Transformation in Higher Plants, 1986, R. T. Fraley, S. G. Rogers, and R. B. Horsch, *CRC Crit. Rev. Plant Sci.*, 4:1-46); and the retroviral vectors for animal cells (Prospects for Gene Therapy, 1984, F. W. Anderson, *Science*, 226:401-409).

Retroviruses (RNA viruses) can be used to deliver genes into animal cells. When the virus enters the cells its RNA acts as a template for reverse transcription of complementary DNA which will integrate into the genome of the host cell. This DNA can be isolated and inserted into a plasmid. This plasmid, with additional genes added, can be used to transform cells with the aid of helper retroviruses.

However, these systems are frequently difficult to control. The problem with using infectious agents such as DNA delivery systems is several-fold. First, infectious agents have limited host ranges. The mediation can only be done on an individual cellular level, typically with somatic tissues, which then must be regenerated artificially into a whole plant. This limits the applicability of Agrobacterium-mediated genetic transformation to those crop species which can readily be regenerated from types of tissues which are susceptible to Agrobacterium infection; the natural host range of Agrobacterium includes only dicotyledonous plants and a limited number of monocot species of the Liliaceae family. Likewise, retroviruses, and the expression of the DNA that they deliver, tend to be host and tissue specific.

Second, infectious agents add an additional level of complexity to the delivery process by introducing a second living system with all its concomitant complications. For example, Agrobacterium-mediated transformations may generate somoclonal variants, which spontaneously arise in plant tissues in tissue culture and which may complicate identification of transformants. In addition, infectious agents such as retroviruses are potentially dangerous—they may harm the organism being modified, or they may lead, through recombination, to the evolution of new pathogens.

Relatively recently, Sanford et al. developed a method whereby substances can be delivered into cells of intact tissues via a particle bombardment process. (High-velocity Microprojectiles for Delivering Nucleic Acids into Living Cells, 1987, T. M. Klein, E. D. Wolf, R. Wu and J. C. Sanford, *Nature*, 337; and Delivery of Substances into Cells and Tissues using a Particle Bombardment Process, J. C. Sanford, T. M. Klein, E. D. Wolf, and N. Allen, *Particular Sci. and Technol.*, 5:27-37). These references teach that small, high-density, tungsten particles (microprojectiles) may be accelerated to high velocity by a particle gun apparatus. An appealing feature of the particle bombardment process is that, compared to prior art devices, it allows for the treatment of relatively many cells at once.

Sanford et al. teach that they have accelerated microprojectiles to sufficient velocities to allow plant cell penetration via the following embodiments (1) a macroprojectile (plastic bullet) and stopping plate, (2) a transferred mechanical pulse, (3) a gas (e.g., air) discharge, and (4) a centripetal acceleration system.

While the particle gun apparatus represents a proposed advance in the art, its various embodiments of the particle bombardment process have certain deficiencies. For example, in each of the various embodiments, the tungsten load suspension amount is not easily reproducible; and it is a rather laborious procedure to inoculate cultures repeatedly. Additionally, in the macroprojectile embodiment (1) and the gas discharge embodiment (3), the velocity must vary with inevitable differences in the firing characteristics; and the suspension velocity is not directly measured. Finally, the macroprojectile embodiment (3) has the following additional differences: the plastic bullet's inertia impairs velocity—making a powerful explosion necessary; the velocities are not easily changed or controlled; and the combustion gases from the gunpowder could be problematical.

Therefore, the development of a technique that can efficiently deliver noncellular biological material directly into living cells and tissues would be beneficial.

It is thus an object of the present invention to provide an apparatus and method for the acceleration of propellable matter.

It is thus another object of the present invention to provide an efficient and practical method and apparatus for inserting a wide range of noncellular biological material directly into living cells and tissues.

SUMMARY OF THE INVENTION

These benefits and other advantages in accordance with the present invention in one embodiment are achieved in an apparatus comprising (a) a source of gas under pressure having an outlet; (b) a propellable matter reservoir having an inlet and an outlet; and (c) a multipurpose valve providing selective communication between the outlet of the source of gas under pressure and the inlet of the propellable matter reservoir.

In another embodiment, the apparatus comprises (a) a source of gas under pressure having an outlet; (b) a source of propellable matter having an outlet; (c) a propellable matter reservoir having an inlet and an outlet; (d) a multipurpose valve, said multipurpose valve providing selective communication between either the outlet of the source of gas under pressure or the outlet of the source of propellable matter, and the inlet of the propellable matter reservoir; and (e) a delivery means having an inlet and an outlet, wherein the inlet of the delivery means is in fluid communication with the outlet of the propellable matter reservoir.

In yet another embodiment, the apparatus comprises (a) a source of gas under pressure having an outlet; (b) a source of propellable matter having an outlet; (c) a propellable matter reservoir having an inlet and an outlet; (d) a delivery means having an inlet and an outlet; (e) a recovery means having an inlet; and (f) a multipurpose valve, said multipurpose valve providing selective communication between either the outlet of the source of gas under pressure or the outlet of the source of propellable matter, and the inlet of the propellable matter reservoir; and providing selective communication between the outlet of the propellable matter reservoir and either the inlet of the delivery means or the inlet of the recovery means.

Also contemplated within the scope of the present invention is a method for accelerating a propellable matter, said method comprising the following steps: (a) providing a predetermined volume of gas having a selected gas pressure; (b) providing a predetermined quantity of a propellable matter, wherein the propellable matter is cellular or noncellular biological material suspended in a carrier medium; and (c) directly contacting said propellable matter with the predetermined volume of a gas, wherein the propellable matter is accelerated at a selected target.

BRIEF DESCRIPTION OF THE DRAWINGS

Further features and advantages of the present invention will become more apparent from the following specification taken in connection with the drawings wherein:

FIG. 1 is a schematic representation of an apparatus in accordance with one embodiment of the invention.

FIG. 2 is a schematic representation of a valve for use with the apparatus of FIG. 1 and in accordance with the invention.

FIG. 3 is a schematic representation of an embodiment of a source of gas under pressure for use with FIG. 1 and the apparatus of the present invention.

FIGS. 4A and 4B are schematic representations of various embodiments of a source of propellable matter for use with the apparatus of FIG. 1 and in the present invention.

FIGS. 5A, 5B and 5C are schematic representations of a delivery and sighting means for using with an apparatus such as indicated in FIG. 1 and in accordance with the invention.

FIG. 6 is a schematic representation of an exemplary embodiment of a velocity detection means for use with the present invention.

FIG. 7 is a schematic representation of synchronizing means for use with an apparatus such as indicated in FIG. 1 and in accordance with the invention.

FIGS. 8A and 8B are schematic representations of an electric circuit as used with the velocity detection means depicted in FIG. 6 hereof, as hereinafter described in the "Examples" section.

FIG. 9 is a graphical representation of the raw data used to measure time of flight of the propellable matter by the electronic circuit hereof, as hereinafter set forth in the "EXAMPLES" section.

DETAILED DESCRIPTION OF THE ELEMENTS OF THE PRESENT INVENTION

The present invention is generally directed to the method and apparatus of accelerating propellable matter. It should be understood that the invention is not limited to a method or apparatus for the propulsion of a specific material, but rather the present invention may be used for the propulsion of many types of materials.

The invention is, however, principally adapted to a method and apparatus for the acceleration of a suspension of biological and nonbiological material into biological cells.

Generally, the nonbiological material will be suitable for therapy or diagnostics. Nonbiological materials include visible dyes, fluorescing compounds, radiosotopes and various metals.

The biological material may be cellular or noncellular. The biological material may be relatively small, preferably less than about 1 micron, more preferably less than about 0.1 micron. Generally, the amount of biological material employed will be up to about 5 micrograms ($\mu g$), with specific amounts possibly varying based upon the type of cellular material used.

By "noncellular biological material" is meant to include viruses (tobacco mosaic virus (TMV), cauliflower mosaic virus (CAMV), maize streak virus (MSV), etc.); organelles (e.g., mitochondria, nucleus, chloroplast or plastid); genetic material, (e.g., either ribonucleic acid (RNA) or deoxyribonucleic acid (DNA), in the form of plasmids or single or double strands); proteins (antibodies or enzymes), or stains.

When DNA is the noncellular biological material, the DNA sequence can be chimeric, but full intact nonchimeric genes from other plant species or lines of the same species may also be used. The DNA may be constructed in a vector appropriate for expression of the exogenous gene in the cells. Suitable transformation vectors include expression vectors.

Vectors suitable for expression generally must include, besides the coding sequence of the desired exogenous gene, appropriate flanking regulatory sequences. Such flanking sequences include a suitable promoter capable of promoting transcription and expression in vivo in cells and a translation terminator capable of signaling the end of transcription or the appropriate processing of the RNA in such a fashion that will allow suitable translation of messenger for protein synthesis.

When DNA is inserted into living cells, it is preferable to screen the progeny at some stage to select for transformants because not all of the cells will have carrier particles inserted into them and not all cells or progeny will uptake the DNA into their genome. The presence of the desired DNA in the cells can then be established in a wide variety of ways, depending on the nature of the DNA.

The transformation vector may contain a selectable marker to allow for selection of transformed cells. The selectable marker may condition a trait which may be assayed biochemically or a phenotypic trait which may be observed. Clearly, if a non-chimeric intact gene, with flanking regulatory sequences, from the same or another cell is used in the present process, chimeric promoter or control sequences are unnecessary and the gene may be used with its native sequence.

Figure 1:
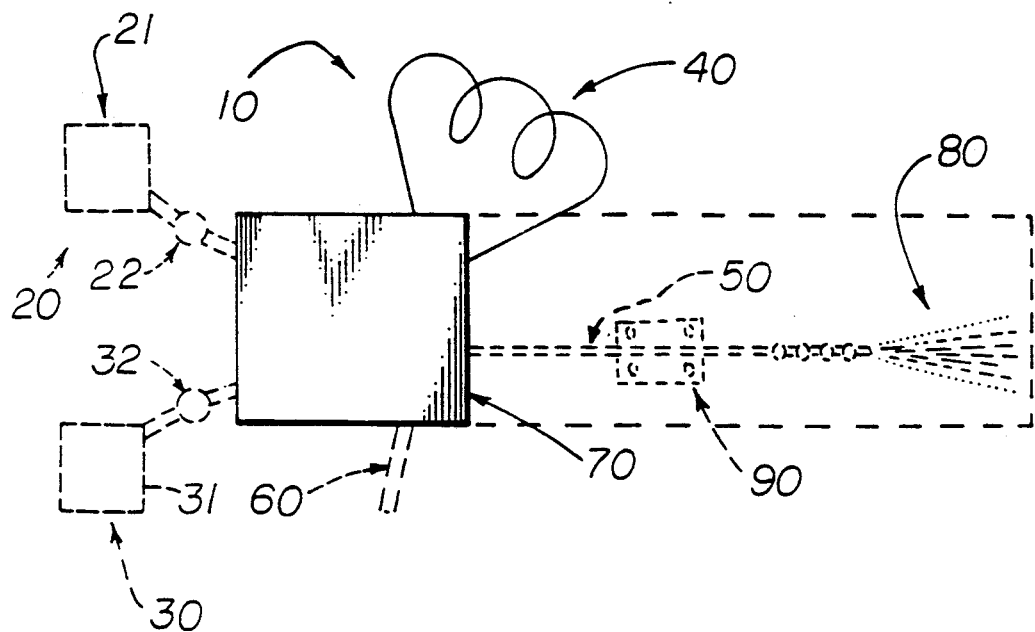

Alternatives to the use of such a selectable marker include suitable morphological or biochemical tests to screen for the transformed progeny. A morphological screening test may be for a dominant phenotypic trait in the progeny. A suitable biochemical screening test is so-called "Southern" blot with a probe hybridizing to the transforming DNA—itself in the genome of the microorganism, plant or animal cells.

The presence of a gene which produces an exogenous product may also be detected by isolation and lysis of the cell and an analysis of the cytoplasm for the exogenous product, or of the nucleus for the exogenous gene. The exogenous product may be detected by electrophoresis, chromatography, immunoassay, or the like. The gene can be detected conveniently by hybridization, for example, by using Southern blotting.

By "cellular biological material" is meant individual or multicellular masses of cellular microorganisms, plant cells or animal cells.

As used herein, the term "cellular microorganisms" includes bacteria and protozoans.

As used herein, the term "plant cells" includes cells that are intact in a plant or parts of a plant, e.g., flowers, kernels, ears, cobs, leaves, husks, stalks; plant cell or tissue cultures, which are with or without cell walls or other natural protective coating, e.g., protoplasts; plant calli; plant tissue clumps; subcellular structures; pollen grains; plant meristems; eggs; zygotes; seeds capable of being germinated into a plant.

The plant cells may be derived from any plant species. The term "plant species" is meant to include monocotyledons (e.g., the grasses, and the cereal crops such as maize, rye, barley, wheat, sorghum, oats, millet and rice); and the dicotyledons (e.g., broad-leafed plants such as tobacco, potato and alfalfa).

As used herein, the term "animal cells" includes tissue from mammals, fish, birds, reptiles, and amphibians.

As discussed above, the biological material may be adsorbed on the surface of a carrier particle. The biological material may be adsorbed on the particle by a variety of techniques. For example, the biological material may be prepared by simply being dried onto suitable carrier particles, as described below.

The carrier particles should have a size, shape, and density sufficient to penetrate the cell membrane and/or cell wall, without causing gross physical damage to the cell. Carrier particles that are too small or not dense enough may fail to penetrate certain cells, while carrier particles that are too large or too dense will be lethal to others. Factors other than cell size, such as the presence of a cell wall or abundance of intracellular nuclei, may also affect the efficiency of transformation by projectiles of a selected size or density.

Generally, the carrier particles have a diameter of between about 0.1 micron and about 100 microns; preferably between about 0.5 micron and about 5 microns. Generally, the carrier particles have a density of between about 1 gram/centimeter$^3$ (gm/cm$^3$) and about 25 gm/cm$^3$; preferably between about 10 gm/cm$^3$ and about 25 gm/cm$^3$.

The carrier particles may be made of a biologically inert dense material. Exemplary materials include certain metals, e.g., tungsten, gold, platinum, palladium, silver and nickel, latex, glass, ceramic, surgical alloys, and ferrite crystals.

In another embodiment of the carrier particles, the biological material may also be encapsulated by inert materials. An exemplary encapsulating agent is polylysine (molecular weight 200,000). The encapsulating agent is applied to the particles by rinsing the particles in a solution of encapsulating agent and then air drying or heat drying the particles thus coated. Once the carrier particles are coated with an encapsulating agent and have been properly dried, the biological material can then be loaded onto the particles. Alternatively, encapsulation of the biological material could be accomplished in conjunction with precipitation of the material onto the particles.

Additionally, the cellular biological material, either procaryotic or eucaryotic, may be frozen, suspended in the carrier medium, and be used as projectiles for acceleration directly at the target matter.

The invention, however, is not be limited to the use of carrier particles with the propelled, biological material. The propelled, biological materials might be frozen, suspended in the carrier medium, and themselves be used as projectiles for acceleration directly at the target matter.

Any carrier medium which is not harmful to the propelled, biological material is suitable as a carrier medium. The carrier medium should be selected to have a flow property effective to convey the carrier particles within it. The flow property of the carrier medium is dependent upon the density, surface tension, effective volume, and viscosity of the propellable matter.

Generally, the carrier medium should have a density which is effective to maintain the particles within it as it moves. Preferably, the density of the carrier medium should be between about 0.5 and about 2.0 g/cc.

Generally, the carrier medium should have a surface tension which is effective to maintain cohesive behavior. Preferably, the surface tension of the carrier medium should be between about 20 and about 80 dynes/cm.

Generally, the carrier medium should have a volume which is effective to suspend a desired number of carrier particles. Preferably, the volume of the carrier medium should be between about 0.5 microliter ($\mu$l) and about 1000 $\mu$l, more preferably between about 5 $\mu$l and about 100 $\mu$l.

Generally, the carrier medium should have a viscosity which is effective to maintain a cohesive propellable volume and suspend the particles. Preferably, the viscosity of the carrier medium should be between about 0.1 centipoise (cp) and about 10 cp, most preferably between about 0.5 cp and about 2 cp.

Preferably, the carrier medium will be capable of suspending the cellular or noncellular biological material, and optionally the carrier particles. Exemplary carrier mediums include liquids, such as water, ethanol, buffer solutions, including phosphate, citrate and acetate buffers; salt solutions, including chlorides or potassium, sodium and calcium; glycols, glycerines and fluorinated hydrocarbons; and liquid nitrogen when the cellular or noncellular biological material is frozen.

Suitable target matter may be cellular biological material; or noncellular biological material, each of which is described above.

The target matter may be cultured in a variety of mediums. Generally, the medium selected should support cell life (support the target material during impact of microparticles).

When the target matter is cellular biological material, the cells may be cultured in any medium capable of sustaining cell metabolism and growth. Exemplary cultures are taught in A Revised Medium for Rapid Growth and Bioassays with Tobacco Tissue Cultures, T. Murashige and F. Skoog, 1962, *Physiol. Plantarum*, Vol. 15, pp. 473–496; and Medium Techniques for Induction and Growth of Monocotyledonous and Dicotyledonous Plant Cell Cultures, R. Schenk and A. Hildebrandt, 1972, *Canadian Journal of Botany*, Vol. 50, pp. 199–204.

A layer of oil may be applied over the cells to control the hydraulic pressure of the medium and to improve cell viability by helping to seal lesions after penetration. For example, the living cells may be bathed in isotonic solution in order to maintain, at the moment the membrane is punctured, the balance of the osmotic pressure of the intercellular matter and the extracellular solution in the zone of the cell membrane puncture. Calcium ions may be present as a membrane stabilizing agent in all these solutions so that the damaged portion of the membrane may quickly be restored. Exemplary isotonic solutions include solutions commonly used for microinjection techniques for plant cells; Ringer solution for cells of cold-blooded animals, protozoa and microorganisms; and Ringer-Locke, Ringer-Tirode and other solutions for cells of animal cells.

When the target matter is noncellular, biological material, it may be cultured/supported in any manner capable of supporting it during impact of the microparticles.

Bombardment of the target matter may cause a portion of the sample to be lost due to dispersal upon impact of the projectile preparation on the suspension of the target matter. Exemplary support means to hold the target matter in place include filter paper, agar medium, metal screens, and metal screen cages. For example, subsequent incubation and staining of the cellular biological material may be performed directly on the filter paper. In another embodiment, both target matter and propellable matter could be put in solution and bombarded with uncoated carrier particles, which are suspended in the carrier medium. Such carrier particles may pull, in their wake, a given volume of the external solution containing noncellular biological material into the cellular biological material.

REFERENCE TO THE DRAWINGS

The apparatus of the present invention may be of any suitable design capable of permitting a predetermined selected volume of gas having a selected gas pressure to contact and accelerate a predetermined amount of a propellable matter towards a selected target matter.

Various embodiments of an apparatus within the scope of the present invention, and set forth in the Figures, are set forth below. As will be apparent from the embodiments, the apparatus of the present invention may be constructed in various forms, permitting, for example, use on a benchtop or as a handheld unit.

In FIG. 1 there is schematically depicted an apparatus, generally designated by the reference numeral 10, which comprises a mutlipurpose valve 70 having inlets and outlets; a source of gas under pressure 30 having an outlet; a optional source of propellable matter 20 having an outlet; a propellable matter reservoir 40 having an inlet and an outlet, an optional delivery means 50 having an inlet and an outlet; and an optional recovery means 60 having an inlet and an outlet.

Multipurpose valve 70 is selected to have a design capable of being adjusted to provide selective communication between either the source of gas under pressure 30 or, optionally, the source of propellable matter 20, and the propellable matter reservoir 40. Mutlipurpose valve 70 is also selected to have a design capable of being adjusted to provide selective communication between the propellable matter reservoir 40, and either the delivery means 50 or, optionally, the recovery means 60.

As seen in FIG. 2, one embodiment of the multipurpose valve 70 may comprise a first subvalve **70*a* and a second subvalve 70*b*. The first subvalve 70*a* provides selective communication between either the outlet of the source of gas under pressure 30 or the outlet of the source of propellable matter 20, and the inlet of the propellable matter reservoir 40. The second subvalve 70*b* provides selective communication between the outlet of the propellable matter reservoir 40, and either the delivery means 50 or the inlet of the recovery means 60**.

Exemplary first subvalve **70*a* and second subvalve 70*b*** may each be one three-port valve or two two-port valves, provided that the two-port valves optionally are in operative combination with a common actuator or different actuators (not shown).

The first and second subvalves may be in operative combination with a common actuator or different actuators.

The actuators of the first and second subvalves are selected to provide switching of pressurized supplies to the valve. Generally, any actuator capable of producing linear or rotary motion may be used. Exemplary actuators include double-acting pneumatic units operated with rack-and-pinion gearing. When different actuators are used, the actuators may be synchronized by timing means (not shown). Exemplary timing means include multipole switches combined with pilot solenoids or common actuating shafts.

Preferably, the actuators are in operative combination with a foot pedal (not shown), thereby simplifying the operation and increasing the relative throughput of the apparatus.

Generally, the propellable matter reservoir 40 may be selected from any number of containers, such as a tube. The propellable matter reservoir 40 may preferably have an inner surface selected to define an inner space with an aspect ratio sufficient to assure uniform ejection of the propellable matter and to assure minimum hang up. Generally, the propellable matter reservoir 40 will be capable of holding between about 0.005 milliliter (ml) and about 100 ml of propellable matter.

Generally, the propellable matter reservoir 40 will be fabricated of a material physically strong enough to be charged with propellable matter from the source of propellable matter 20 and gas from the source of gas under pressure 30, without becoming physically deformed. Preferably, the propellable matter reservoir 40 will be fabricated of a material which is capable of withstanding at least 1000 pounds per square inch (psi) pressure at physiological temperatures. An exemplary material for use in fabricating the propellable matter reservoir is stainless steel.

Figure 2:
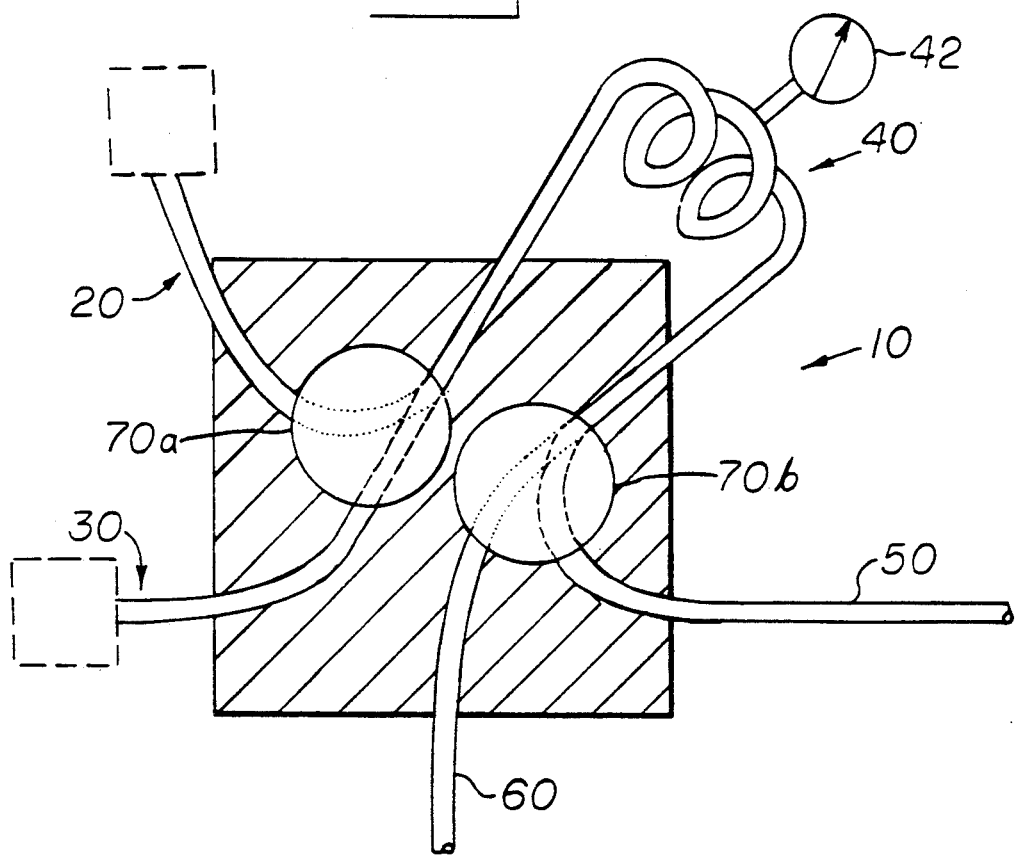

As seen in FIG. 2, the temperature within the propellable matter reservoir 40 may be controlled by temperature control means 42. Exemplary temperature control means include thermocouples implanted in a block heater surrounding the propellable matter reservoir 40.

Although the schematic representation in FIGS. 1 and 2 show the use of only one source of propellable matter, the principles set forth in the operation of the apparatus 10 may be readily applied to the propulsion of two or more types of propellable matter, from a plurality of sources of propellable matter.

Generally, the volume of propellable matter 20 in the propellable matter reservoir 40 may be controlled by any means that provides measured, reproducible samples of propellable matter 20. Conventionally, when tubing or the like is used, one tube capable of holding a first volume may be replaced with another tube capable of holding a second volume. However, the apparatus is not intended to be so limited. For example, a level sensor (not shown) may be positioned at any location effective to provide accurate, reproducible measurements of the volume of propellable matter in the propellable matter reservoir 40.

As seen in FIG. 1, the source of gas under pressure 30 may comprise a gas supply means 31, and, optionally, a gas regulating means 32. The source of gas under pressure is selected to provide predetermined volumes of gas into the propellable matter reservoir 40. The gas pressure is dependent upon the type of gas employed and the volume of the gas. Generally, the gas pressure will be between about 15 atmospheres (atm) and about 150 atm.

The source of gas under pressure 30 may be regulated by any means which is capable of providing gas at a desired pressure into the propellable matter reservoir 40. The gas regulating means may be manually or automatically operated.

Preferably, the source of gas under pressure 30 will be capable of continually providing volumes of gas to the propellable matter reservoir 40, to permit relatively quick, repeated actuations of the apparatus 10.

Figure 3:
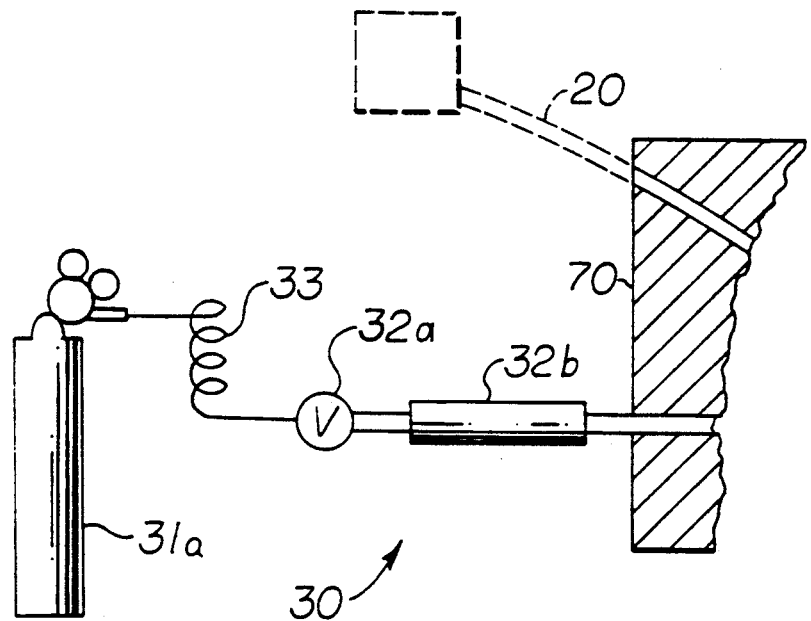

An exemplary source of gas under pressure 30 is further set forth in FIG. 3. As shown in FIG. 3, the source of gas under pressure 30 comprises (1) a gas supply means 31 in the form of a gas supply tank 31a having an outlet, (2) a gas supply line 33 having an inlet and an outlet; and (3) a gas regulating means 32 in the form of a gas valve 32a, and a gas reservoir 32b having an inlet and an outlet.

The outlet of the gas supply tank 31a is in pneumatic communication with the inlet of the gas supply line 33. The outlet of the gas supply line 33 is in turn in selective pneumatic communication, via gas valve 32a, with the inlet of the gas reservoir 32b.

Exemplary gas supply means 31 include gas cylinders and tanks.

The gas reservoir 32b may be selected from any number of containers, such as a tube. Generally, the gas reservoir 32b will be capable of holding between about 1 ml and about 100 ml of gas.

Generally, the gas reservoir 32b may be fabricated of a material physically strong enough to be charged with gas from the source of gas under pressure 30 without becoming physically deformed. Preferably, the gas reservoir 32b will be capable of withstanding up to about 150 atmospheres (atm) of gas pressure. Exemplary materials for use in fabricating the gas supply line include stainless steel.

The gas should be selected to have a molecular weight sufficiently low to allow rapid enough expansion to produce the requisite particle velocities. Generally, the molecular weight of the gas should be between about 2 and 40 atomic mass unit (amu). Exemplary gases include helium, hydrogen, and air.

As stated above with reference to FIGS. 1 and 2, the apparatus preferably comprises a source of propellable matter 20 in selective fluid communication with the propellable matter reservoir 40. Obviously, when the source of propellable matter 20 is not present, the propellable matter reservoir 40 will be manually filled and affixed in fluid communication with the apparatus.

Figure 4A:
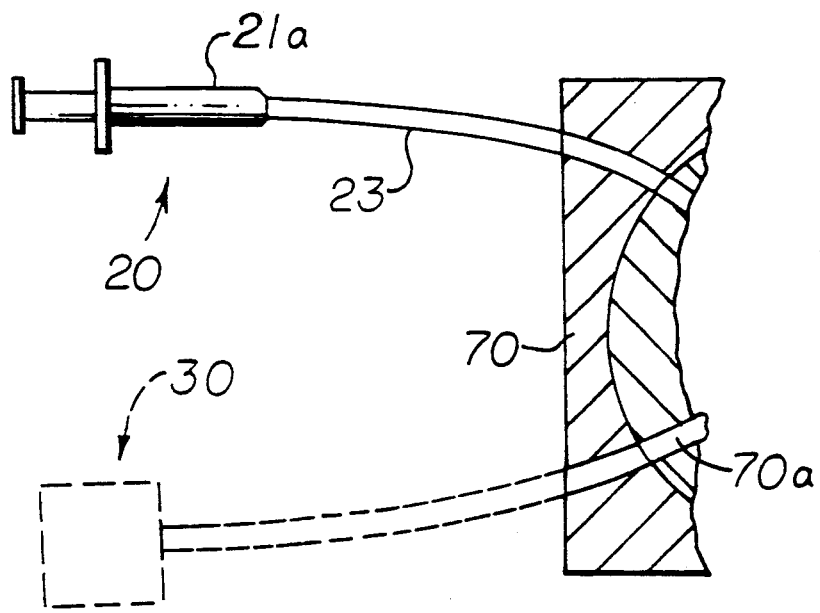
Figure 4B:
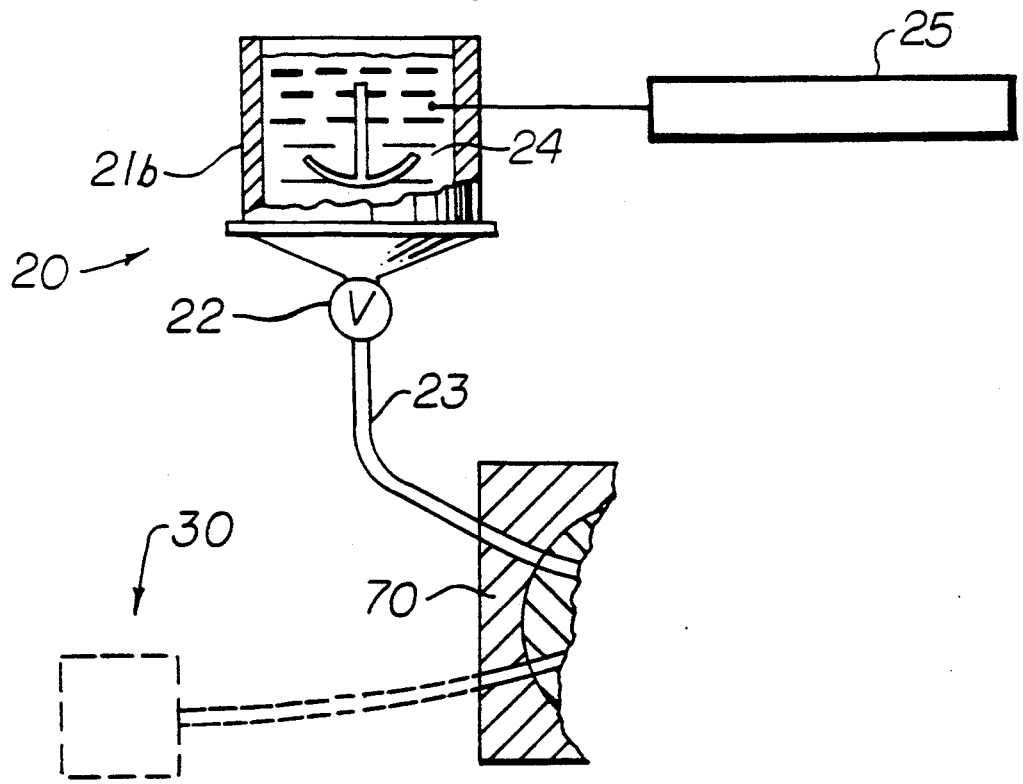

As seen in FIG. 1, and as particularly shown in FIGS. 4A and 4B, the source of propellable matter 20 is capable of providing predetermined volumes of propellable matter into the propellable matter reservoir 40.

Preferably, the source of propellable matter 20 will be capable of continually providing selected volumes of propellable matter to the propellable matter reservoir 40, to permit relatively quick, repeated actuations of the apparatus 10. The source of propellable matter 20 comprises a propellable matter supply means 21. Exemplary propellable matter supply means 21 include syringes, tanks, tubing or other conduits. Generally, the propellable matter supply means 21 will be fabricated of a material which is capable of being sterilized. Exemplary materials include stainless steel and polytetrafluoroethylene.

Depending upon the inherent regulating capacity of the propellable matter supply means, the apparatus may comprise means capable of regulating the flow of propellable matter, i.e., propellable matter regulating means 22. The propellable matter regulating means may be in operative combination with the propellable matter supply means 21 to permit a selected volume of propellable matter to be provided into the propellable matter reservoir 40. Exemplary propellable matter regulating means include valves and pumps.

As previously indicated, exemplary embodiments of the source of propellable matter 20 are set forth in FIGS. 4A and 4B. These embodiments depict sources of propelled material which are capable of having a selected volume of propellable matter discharged therefrom.

In one embodiment, as seen in FIG. 4A, the source of propellable matter comprises (1) propellable matter supply means 21 in the form of a syringe 21a having an outlet, and (2) a propellable matter supply line 23 having an inlet and an outlet. The outlet of the syringe 21a is in selective fluid communication with the inlet of the propellable matter supply line 23. The outlet of the propellable matter supply line 23 is in turn in fluid communication with an inlet of multipurpose valve 70 leading to the propellable matter reservoir 40.

In another embodiment, as seen in FIG. 4B, the source of propellable matter comprises (1) propellable matter supply means 21 in the form of a propellable matter supply tank 21b having an outlet (2) a propellable matter regulating means 22 in the form of a propellable matter valve 22 and (3) a propellable matter supply line 23 having an inlet and an outlet. The outlet of the tank 21b is in selective fluid communication, via propellable matter valve 22, with the inlet of the propellable matter supply line. The outlet of the propellable matter supply line 23 is in turn in communication with an inlet of valve 70 leading to the propellable matter reservoir 40.

Depending upon the time that the propellable matter is maintained in the propellable matter supply tank 21b, the propellable matter supply tank 21b may be in operative combination with a temperature control means 25 as shown in the alternate embodiment of FIG. 4B to maintain the propellable matter at a desired temperature. Exemplary temperature control means include thermocouples implanted in a block heater surrounding the propellable matter supply tank 21b.

Depending upon the relative viscosity of the carrier medium, the propellable matter supply tank 21b may be in operative combination with an agitation means 24, to maintain the particles in suspension in the carrier medium. Obviously, the choice of agitation means will depend upon the type of propellable matter supply tank employed. Exemplary agitation means include reciprocating syringe pumps, magnetic stir bar agitation, valving arrangements and pumps to create alternating directions of flow within the propellable matter supply tank 21b. Preferably, the agitation means will be selected so as also to provide alternating directions of flow within the propellable matter reservoir 40, e.g. a reciprocating syringe pump.

As seen in FIGS. 1 and 2, the outlet of the propellable matter reservoir 40 may be in selective communication, via multipurpose valve 70, with the inlet of recovery means 60.

The recovery means 60 allows for overflow of excessive propellable matter from the propellable matter reservoir 40. Recovery means 60 includes any means for capturing propellable matter. A preferred recovery means comprises a tube which is sealed from which material is drawn out. Such a design also permits an open system to which an agitation means, e.g., a reciprocating syringe pump, may be selectively combined to provide alternating directions of flow within the propellable matter reservoir 40.

The recovery means 60 may be fabricated of any material which is capable of containing and not having a deleterious effect upon the propellable matter. Preferably, to avoid overflow of significant quantities of suitable propellable matter from the propellable matter reservoir, the recovery means 60 may be made of a transparent material to allow easy measurement of the material therein. Exemplary materials capable of visual inspection of overflow include polytetraflouroethylene (PTFE).

Delivery Means

As seen in FIGS. 1, 2, and 7 the outlet of the propellable matter reservoir 40 may be in selective communication, via multipurpose valve 70, with the inlet of delivery means 50.

Figure 5B:
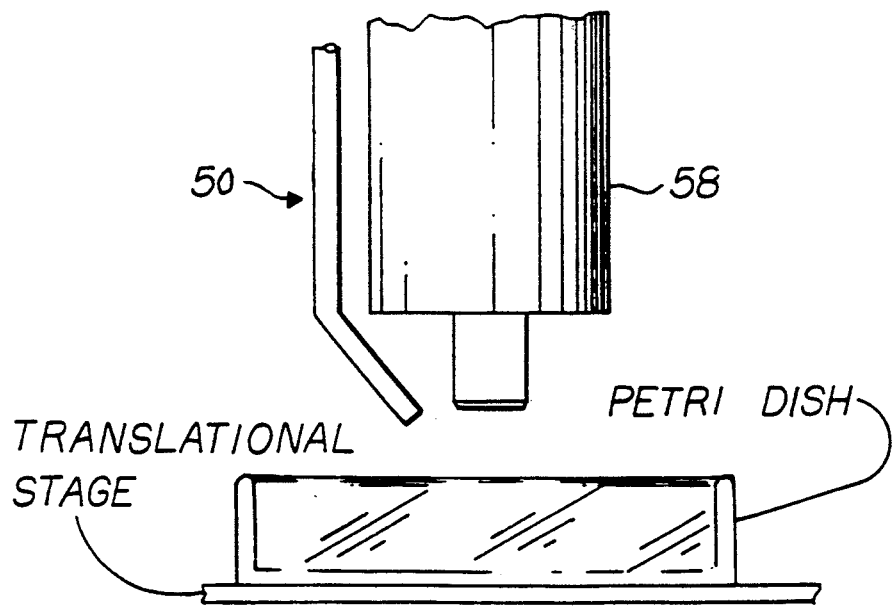
Figure 5A:
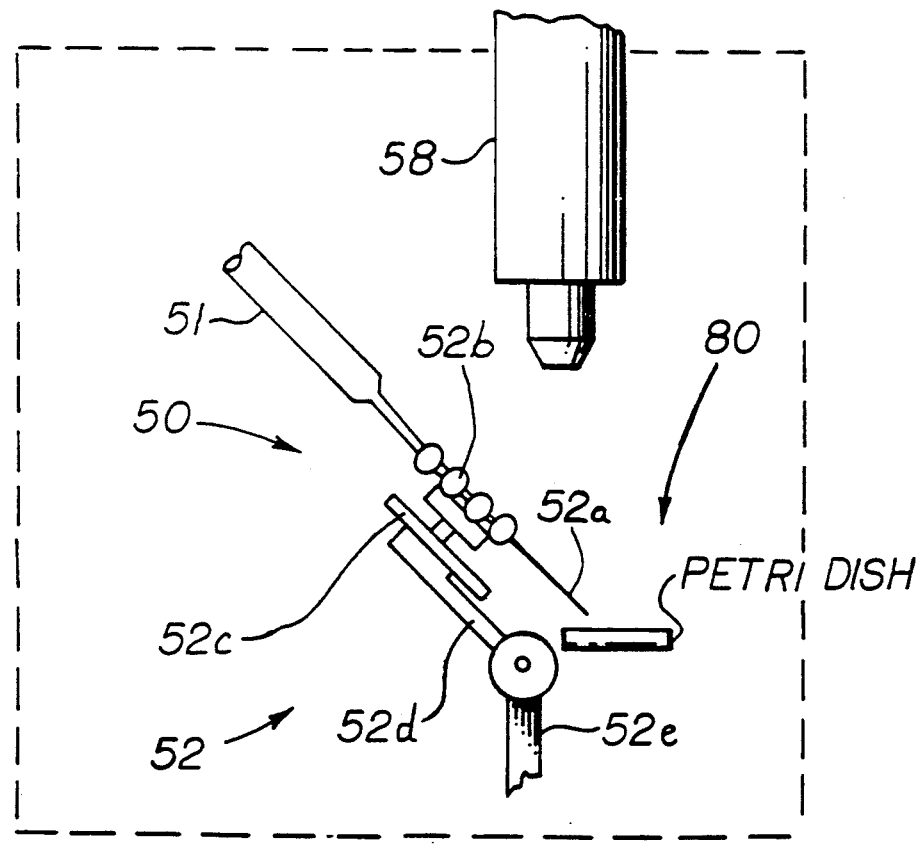
Figure 5C:
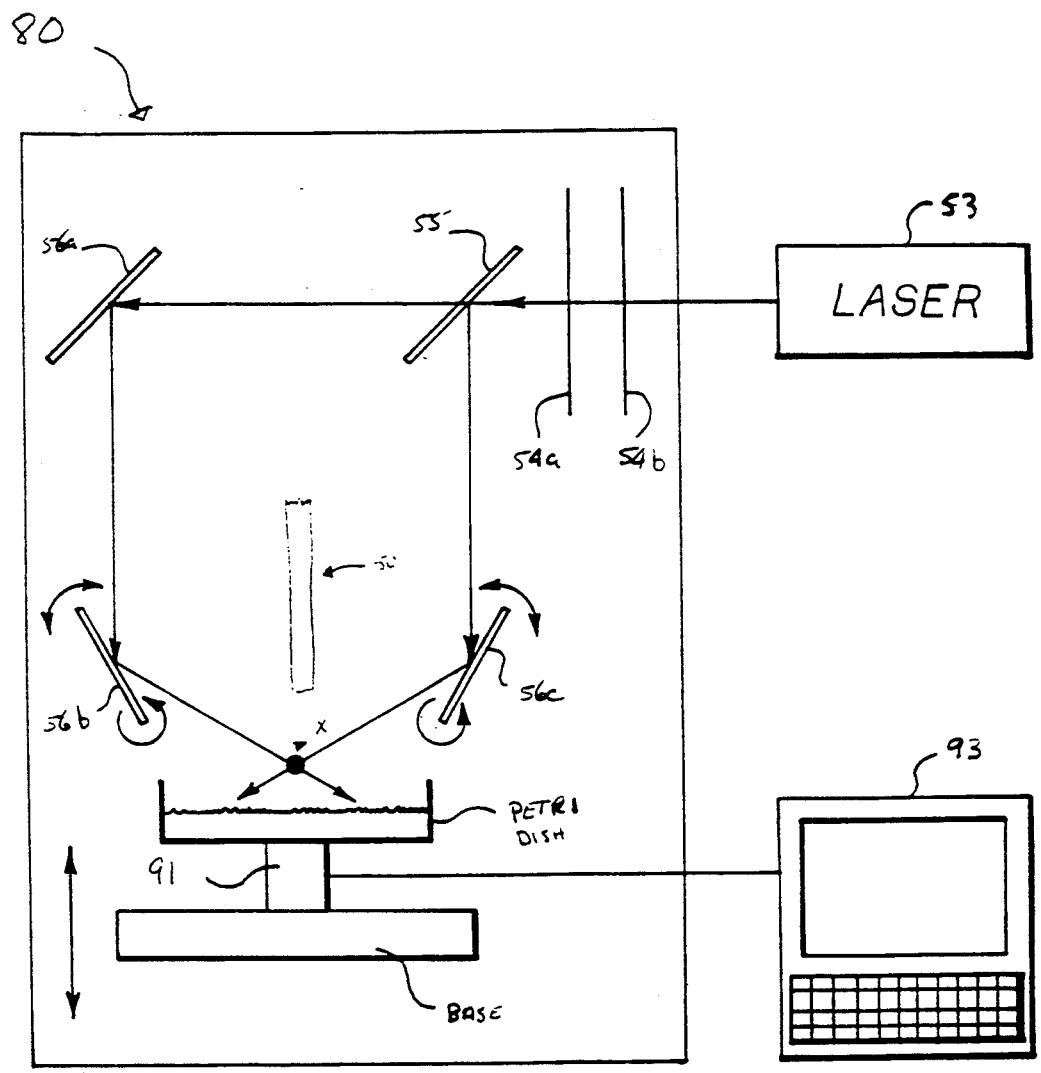

The delivery means, particularly as shown in FIGS. 5A, 5B and 5C, may comprise a macroaiming means 51 and/or a microaiming means 52. Because of the force of the propellable matter exiting from the propellable matter reservoir 40 (shown in FIGS. 1 and 2), it is preferred that when the delivery means 50 comprises microaiming means 52, it also comprises macroaiming means.

As seen in FIG. 5A, the macroaiming means 51 in turn is in fluid communication with microaiming means 52.

Generally, the macroaiming means 51 is selected to have an inner surface which defines a bore of a length, geometry and diameter sufficient to prevent substantial loss of acceleration of the propellable matter due to gas bypassing the propellable matter. Preferably, the macroaiming means 51 is a tube selected to have an inner surface defining a generally cylindrical bore with an inner diameter of between about 500 microns and about 2000 microns, preferably about 750 to about 1250 microns.

The macroaiming means 51 may be made of any material capable of maintaining its shape under the conditions of delivery. Exemplary materials include glass, plastic and stainless steel.

When the delivery means consists of only the macroaiming means 51, it may be used to accelerate propellable matter in a so-called "shotgun" firing pattern. When the delivery means comprises microaiming means 52, it allows relatively more precise aiming of the propellable matter.

An advantage of the present device is the ability to selectively aim the delivery means, providing relatively precise aiming of the propellable matter. Although specific ways to aim the delivery means are described below, it will be apparent to a skilled artisan that any manner of aiming the delivery means is readily within the scope of the present invention.

While capable of being visually sighted, the delivery means preferably comprises a sighting means 58. The sighting means 58 should be effective to aim the delivery means 50 at a selected area of the target matter. The choice of specific sighting means being within the discretion of a skilled artisan. Exemplary sighting means include microscopes, boroscopes, and lasers.

It may be beneficial to illuminate the target matter using a lighting means (not shown). While any source of illumination is suitable, fiber optics provide adequate lighting without significantly increasing the temperature in the propulsion zone 80.

When the sighting means is a microscope, it preferably will provide a magnification of between about 10X and about 200X. When the sighting means comprises a boroscope it is preferably in electrical combination with a video monitor.

An exemplary embodiment of the microaiming means 52 is seen in FIG. 5A. The microaiming means 52 comprises a pipette 52a, which is in fluid communication with the microaiming means 51; a microinstrument 52b placed in a holder 52c rigidly connected to a mobile tool 52d of a three-way micromanipulator 52e. The micromanipulator 52e may comprise a joystick (not shown) that controls the position of pipette 52a.

The pipette 52a should be selected to have an internal diameter of sufficient lumen size to pass propellable matter. The internal diameter of the pipette is generally between about 10 microns and about 500 microns, preferably between about 100 to about 250 microns. Pipettes are conventionally prepared from capillary tubing according to well-known techniques (see generally, Microinjection of Early SV40 DNA Fragments and T Antigen, A. Graessman, M. Graessman, and G. Mueller, 1980, In: *Methods in Enzymology*, Vol. 65, Academic Press, New York, pp. 816-825).

Exemplary microaiming means 52 may beneficially be constructed from conventional microinjection devices, which are relatively easily modified to define microaiming means by a skilled artisan.

Conventional microinjection devices and techniques are taught in the following references: U.S. Pat. No. 4,743,548; The "Pricking" Method, F. Yamamoto, M. Furusawa, I. Furusawa, and M. Obinata, 1982, *Exp. Cell. Res.*, 142:79-84; Microelectrode Methods for Intracellular Recording and Ionophoresis, R. D. Purres, 1981, Academic Press, NY; Micro-Injection of Nucleic Acids into Cultured Mammalian Cells by Electrophoresis, Ocho, W. S. Nakai, K. Tasaka, S. Watanabe, and T. Oda, 1981, *Acta Med. Okayama*, 35:381-384; A Method for the Microinjection and Culture of Protoplasts at Very Low Densities, W. A. Lawrence and D. R. Davies, 1985, *Plant Cell Rep.*, Vol. 4, pp. 33-35; Transformation of Plant Cells by Microinjection of DNA, H. H. Steinbiss, P. Stabel, R. Topfer, R. P. Hirtz, and J. Schell, 1984, In: *Proceedings of the 1984 Wye International Symposium, Experimental Manipulation of Ovule Tissue: Their Micromanipulation, Tissue Culture and Physiology*, Wye College, University of London; Protoplast Derived Tobacco Cells Can Survive Capillary Microinjection of the Fluorescent Dye Lucifer Yellow, H. H. Steinbiss and P. Stabel, 1983, *Protoplasm*, Vol 116, pp. 223-227; Capillary Microinjection into Protoplasts and Intranuclear Localization of Injected Materials, H. Morikawa and Y. Yamada, 1981, *Plant Cell Physiol.*, Vol. 26, pp. 229-236; Microinjection of Early SV40 DNA Fragments and T Antigen, A. Graessman, M. Graessman, and G. Mueller, 1980, In: *Methods in Enzymology*, Vol. 65, Academic Press, New York, pp. 816-825; and Photoengraving of Cover Slips and Slides to Facilitate Monitoring of Micromanipulated Cells or Chromosome Spreads, P. F. Lin and F. H. Ruddle, 1981, *Exp. Cell Res.*, Vol 134, pp. 485-488.

In a second exemplary embodiment, as seen in FIG. 5B, the delivery means 50 and sighting means 58 are in operative combination with a translational stage (not shown), for positioning the delivery means relative to the target matter.

In yet a third exemplary embodiment, seen in FIG. 5C, the sighting means may comprise a laser system including a laser for producing a linearly polarized beam which is transmitted through the optical elements of the system and reconverge on a selected spot X. The optical elements, which are positioned between the laser and the target, include pinhole plates, a beam splitter and lens for redirecting and focusing the transmitted beams.

The laser 53 is positioned to emit a nondiverging light beam which is transmitted through the optical elements of the system. The beam is transmitted through two pinhole plates 54a and 54b apertures which allow the beam to pass through the plates. The apertures of the pinhole plates are positioned to permit the nondiverging light to be directed through a conventional beam splitter, wherein partial reflectors divide an incoming beam into at least two beams and direct them in separate paths through the propulsion zone 80. The beams are angled off of mirrors 56a, 56b, and 56c, which are angled to permit the two beams to reconverge on spot X.

As seen in FIGS. 1, 5A, 5B, 5C and 7, the outlet of the delivery means opens into a propulsion zone 80, into which the target matter may be placed. Preferably, the propulsion zone 80 is environmentally controlled.

To assist in the aiming of the delivery means 51, the target matter may preferably be placed on a translational stage capable of positioning the target matter relative to the delivery means.

For example, a vacuum may be drawn in the propulsion zone. The degree of vacuum should be sufficient to avoid decreasing the velocity of the particles due to the reduction caused by air resistance, and to prevent scattering of the propellable matter. Preferably, the degree of vacuum in the propulsion zone may vary from about 0 atmospheres (atm.) to about 0.5 atm.

Generally, the propulsion zone may be defined by a chamber. Suitable chambers include an environmentally-controlled chamber taught in "Fisher 88", Laboratory Equipment Catalog of Fisher Scientific, Inc., Pittsburgh, PA.

Velocity Measuring Means

In another embodiment, the apparatus 10 comprises a velocity measuring means 90 as indicated in FIGS. 1, 5C, 6, and 7. Any device capable of monitoring the velocity of the propellable matter is suitable for use as the velocity measuring means.

Generally, the velocity measuring means may be positioned at any location from which the velocity of the accelerated propellable matter may be reproducibly measured. Preferably, velocity measuring means 90 may be positioned on delivery means 50.

As seen in FIG. 5C, an exemplary velocity measuring means 90 comprises a transducer 91, such as a strain gauge. The transducer is in turn in electronic communication with an analog readout 93. The displacement caused by the impact of the propellable material on the petri dish is translated into a velocity measurement.

Figure 6:
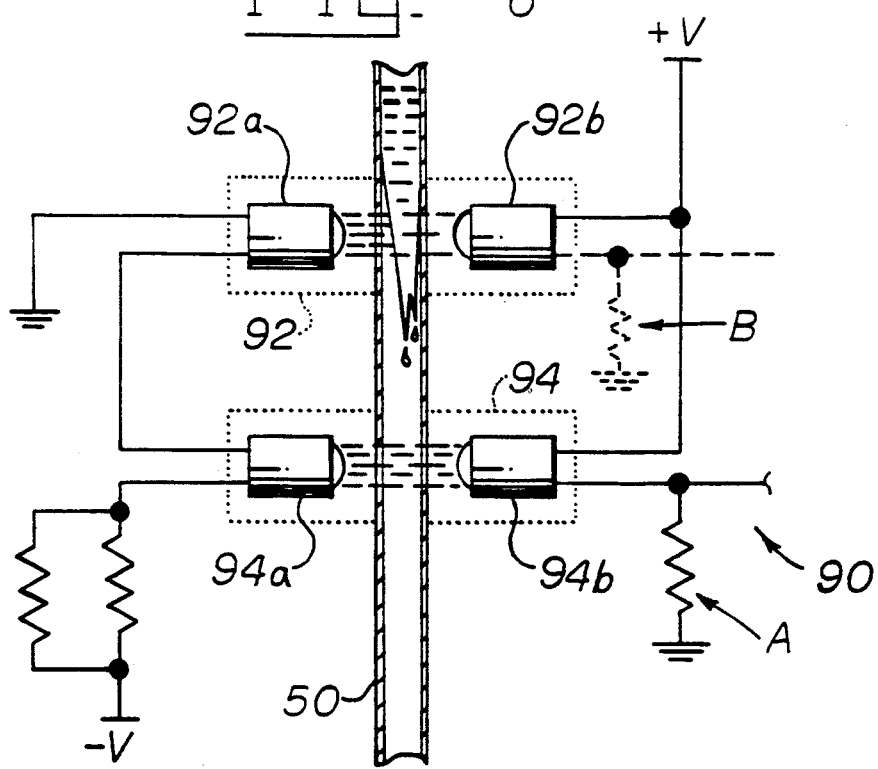

As seen in FIG. 6, another exemplary velocity measuring means 90 comprises a first velocity sensor 92 and a second velocity sensor 94, said sensor being positioned at successive locations across delivery means 50.

The first velocity sensor 92 comprises source means 92a and sensor means 92b. The second velocity sensor 94 comprises source means 94a and sensor means 94b.

Exemplary source means 92a and 94a include infrared emitters, such as infrared light emitting diodes (LED), or any other similar light source. When the source mounting means comprises infrared emitters, the delivery means is beneficially constructed of a transparent material, such as glass or clear plastic.

Exemplary sensor means 92b and 94b include photodiodes, phototransistors, or photovoltaic cells.

Generally, the first and second sensors may be in operative combination via an electric circuit. Preferably, the velocity detection means will be in operative combination with the multipurpose valve 70 via an electric circuit.

Generally, the circuit should provide for the measurement of the time of flight (as seen in the "Examples" section, below, and FIG. 9) between first and second sensors. Preferably, the circuit may provide "sequence timing", to ensure that all parts of the velocity detection means are synchronized with the acceleration of propellable matter. After the circuit has ensured the timing status, the circuit may provide operative communication between the velocity detection means and multipurpose valve 70, whereby a preselected time interval of effective electric power to operate multipurpose valve 70, providing communication between the source of gas under pressure 30 and the propellable matter reservoir 40.

Figure 8A:
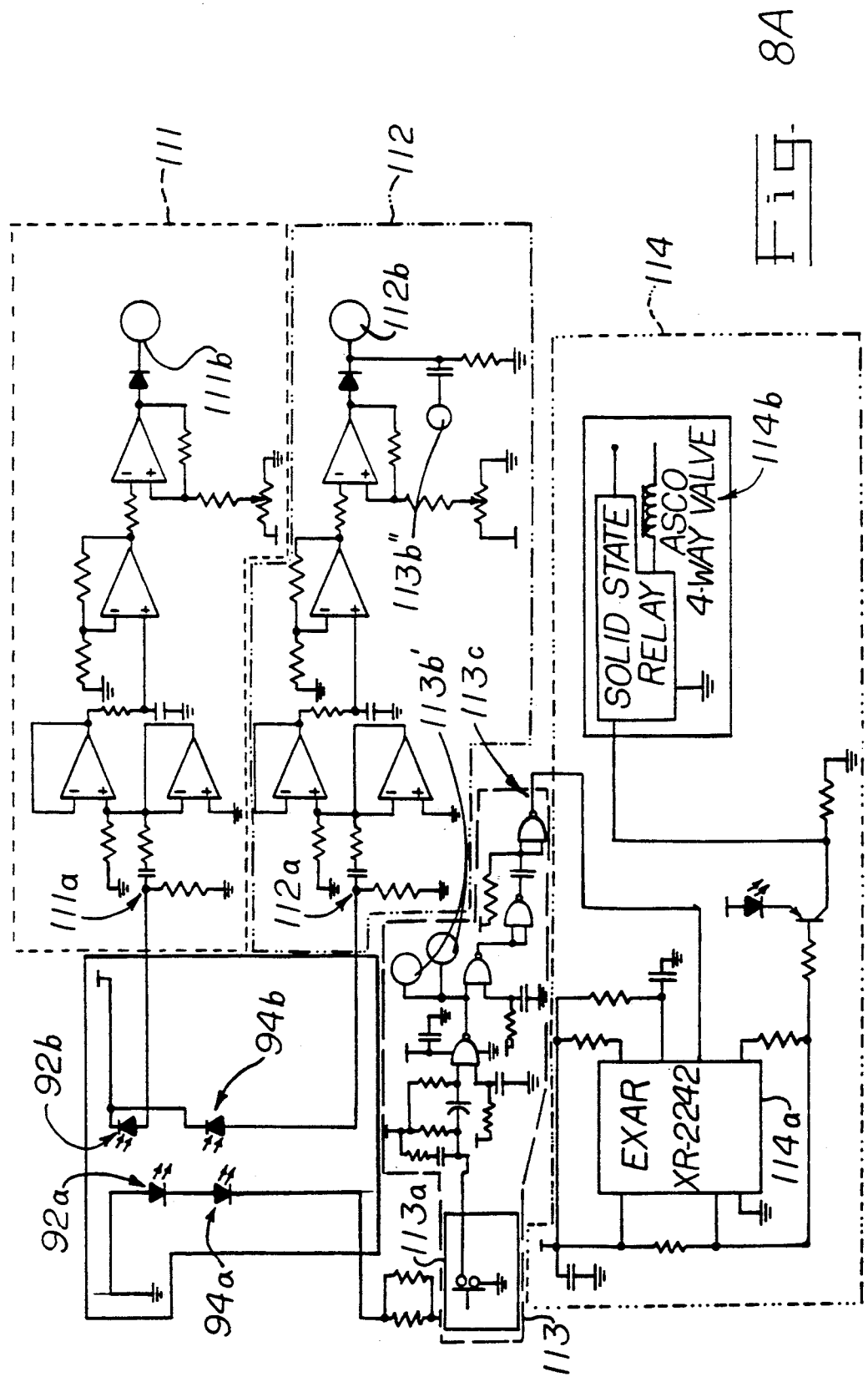
Figure 8B:
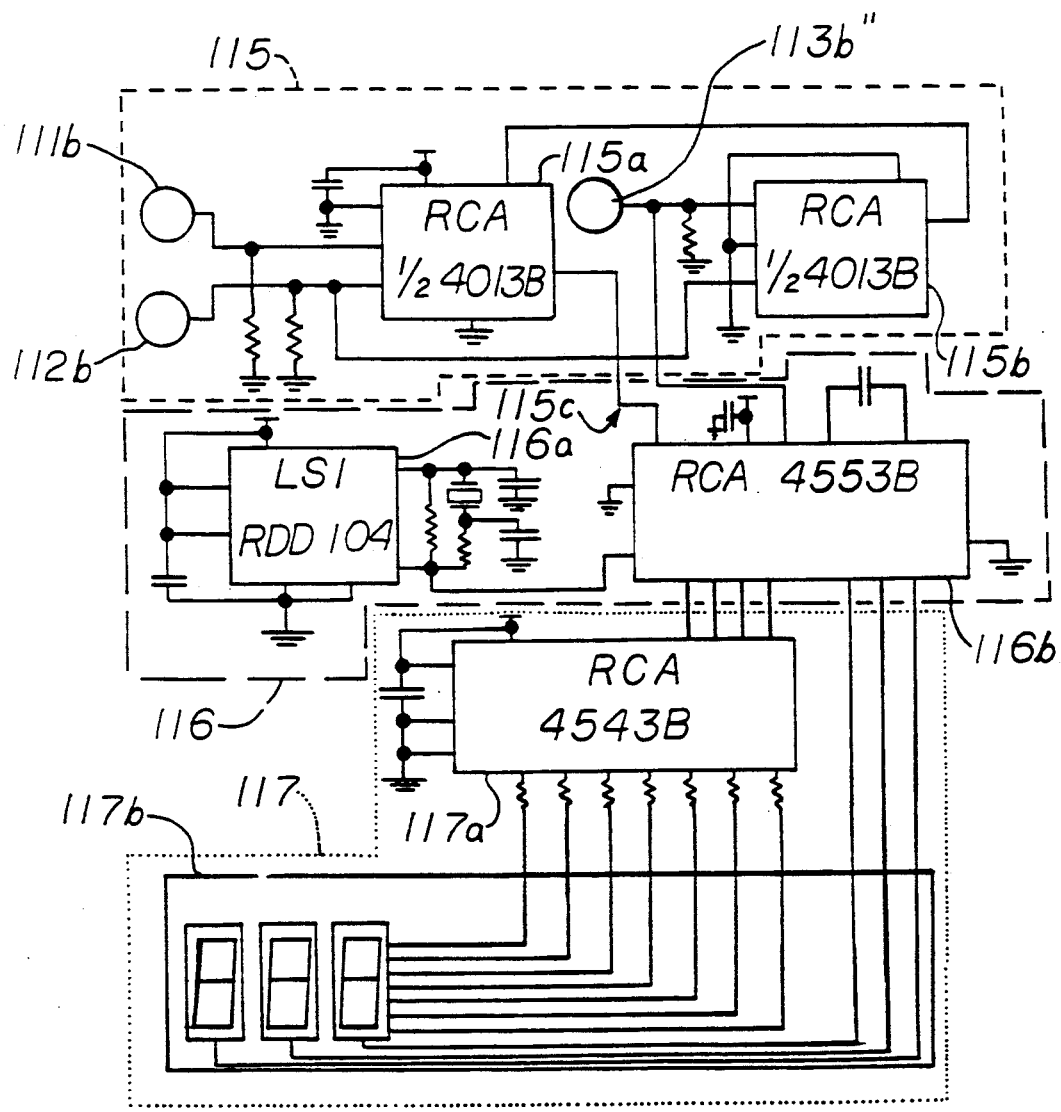

Any number of circuits may be devised by a skilled artisan to achieve the requirements set forth above. Exemplary circuits for the velocity detection means are shown in FIGS. 8A and 8B and will be discussed hereinafter.

Synchronizing Means

In another embodiment as seen in FIG. 7, the apparatus 10 may be in operative combination with a means effective to synchronize at least some elements for loading and accelerating the propellable material. Synchronization of at least some apparatus elements is intended to reduce the number of steps that an operator would have to perform, consequently decreasing the time necessary between actuations and increasing the throughput.

An exemplary embodiment of synchronizing means is set forth in FIG. 7. The synchronizing means 100 comprises a computer 100 being in operative combination with apparatus 10.

The computer 100 is in communication, via line 101, with box 102, having a series of sensor and command leads therefrom.

A first lead 102a may be in sensor and command communication with the temperature control means 25, whereby the temperature of the propellable matter supply tank 21b is automatically regulated.

A second lead 102b may be in sensor and command communication with the agitation means 24, whereby the propellable matter is agitated at a selected rate.

A third lead 102c is in command communication with the propellable matter regulating means 22. The lead maintains the source of propellable matter in an open or closed position.

A fourth lead 102d is in sensor communication with third lead 102c and command communication with multipurpose subvalve 70a. When the source of propellable matter is maintained in the open position, multipurpose valve 70 provides selective fluid communication between the source of propellable matter 20 and propellable matter reservoir 40, and selective fluid communication between the propellable matter reservoir 40 and the recovery means 60.

A fifth lead 102e is in sensor and command communication with the temperature control means 42, whereby the temperature of the propellable matter reservoir is regulated.

A sixth lead 102f is in sensor communication with the fifth lead 102e and command communication with the velocity detection means 90. When a selected volume of propellable matter is in the propellable matter reservoir 40, a timing cycle for the firing of apparatus 10 is initiated.

A seventh lead 102g is in sensor communication with sixth lead 102f and gas valve 32a. When the timing cycle of the velocity detection means is ensured, the gas regulating means is maintained in the open position.

An eighth lead 102h is in sensor communication with the seventh lead 102g and multipurpose subvalve 70b. When the source of gas under pressure is in the open position, the multipurpose valve 70 provides selective pneumatic communication between the source of gas under pressure 30, via the propellable matter reservoir 40, and the delivery means 50.

In ninth lead 102i is in sensor communication with the velocity detection means 90. After a selected volume of gas under pressure is emitted into the propellable matter reservoir 40 and an accelerated volume of propellable matter passes the velocity detection means 90, the velocity of the propellable matter is displayed.

Generally, the synchronizing means may be any process control system which is capable of assimilating data provided by the various sensor leads, and operating the apparatus via the various command leads. Exemplary synchronizing means include single board microcontrollers, or the CAMILE TM (Trademark of The Dow Chemical Company) data acquisition and process control system, commercially available from The Dow Chemical Company.

Operation

The apparatus, as seen in FIG. 1, may be operated as follows. Target matter may be selectively positioned in the propulsion zone at a predetermined distance from the delivery means.

When the propellable matter or target matter includes cellular biological material, the target matter will be selectively positioned at a distance effective to permit contact with the propellable matter which will not be lethal to a substantial number of the cellular biological material (though some cells may die).

Generally, the target matter will be placed at a distance of between about 1 centimeter (cm) and about 100 cm from the outlet of the delivery means.

When the delivery means comprises a macroaiming means, without a microaiming means, the target matter will be placed at a distance of from about 5 cm to about 20 cm to the delivery means outlet. When the delivery means comprises a microaiming means, the target matter will be placed at a distance of about 1 millimeter (mm) to about 100 cm to the delivery means outlet.

The apparatus as generally set forth in FIG. 1, and specifically embellished in selected Figures, may be operated as follows. As seen in FIGS. 1, 2 and 4B, multipurpose valve 70 and propellable matter regulating means 22a are set to provide fluid communication between the propellable matter supply means 21 and the propellable matter reservoir 40. Consequently, propellable matter is allowed to pass from the source of propellable matter 20 and into the propellable matter reservoir 40.

As seen in FIGS. 1 and 2, multipurpose valve 70 is also set to provide fluid communication between the propellable matter reservoir 40 and the recovery means 60. Any volume of propellable matter in excess of the volume of the propellable matter reservoir 40 is released into the recovery means 60.

As seen in FIGS. 1, 2, and 3, multipurpose valve 70 and gas regulating means 32a are then set to provide pneumatic communication between the gas supply means 31 and the propellable matter reservoir 40. Consequently, a selected volume of gas under sufficient pressure to accelerate the propellable matter at a desired velocity is allowed to pass from the source of gas under pressure 30 into the propellable matter reservoir 40.

Multipurpose valve 70 is also set to provide pneumatic communication between the propellable matter reservoir 40 and the delivery means 50. Once the gas is discharged into the propellable matter reservoir 40 it contacts against the propellable matter, which is accelerated into delivery mean 50, if present.

As seen in FIGS. 1 and 6, while in the delivery mean 50 the propellable matter will pass first sensor 92 and second sensor 94. First and second sensors 92 and 94 provide means to record the velocity of the propellable matter, permitting reproducible acceleration of the propellable matter.

Preferably, the propellable matter will be accelerated to an effective velocity. The "effective" velocity desired will vary depending upon the desired results.

Generally, for purposes of introducing biological material into cellular biological material, the velocity of the propellable matter should be effective to cause the biological material to penetrate the cell membrane, and wall if present. Preferably for such systems, the propellable matter should have a velocity at the point of exiting the delivery means of between about 200 miles per hour (mph) to about 1200 mph.

As should be apparent, the velocity of the propellable matter is dependent upon a variety of known parameters. Such parameters include, but are not limited to, the length and inner diameter of the delivery means; the gas pressure; the flow properties of the gas; the flow properties of the propellable matter; the physical properties of the propellable matter; the distance between the outlet of the delivery means and the target matter; and the volume and flow properties of the medium in which the target matter is cultured.

The flow characteristics of the propellable matter are not particularly critical. Thus, the propellable matter may be accelerated in plug flow, or turbulent flow. By "plug flow" it is meant that the propellable matter moves as a generally continuous mass, and the gas and propellable matter zones will not substantially intermix. By "turbulent flow" is meant fluid flow in which the velocity at a given point varies erratically in magnitude and direction, and consequently some mixing of the gas and propellable matter occurs. It turbulent flow occurs, the propellable matter and gas will interact to create a dispersion and consequently provide a broader columnar beam of propellable matter when discharged from the apparatus.

Because the gas under pressure contacts the propellable matter directly and is itself released into the propulsion zone, the propellable matter loaded into the reservoir is reproducibly discharged into the propulsion zone. A minor but reproducible proportion of propellable matter remains in the delivery means. Basically, the only propellable matter which is not discharged into the propulsion zone is that which adheres or wets to the inner walls of the valves and the discharge means. Such propellable matter is referred to as "hang up". The quantity of the hang up will depend upon and vary with the viscosity of the particular propellable matter.

The velocity of the propellable matter is measured as it passes the velocity detection means. More specifically, the time of flight between the first and second sensors of velocity detection means, located on the delivery means, indicates the velocity of the propellable matter.

By providing reproducible measurements of the time of flight of the propellable matter, one of ordinary skill in the art may adjust the various parameters which affect the velocity of the propellable matter. By adjusting the parameters, the skilled artisan may select the optimum velocity of the propellable matter.

A desired volume of propellable matter exits from the delivery means into the propulsion zone.

The operation is completed by selectively setting the multipurpose valve 70 in order to block the flow of gas from the gas reservoir 32 into the propellable matter reservoir.

The previous discussion is intended to provide a general idea of the criteria to be considered in the operation of the apparatus according to the present invention.

Given the teachings above, the selection of operating conditions for each system employed will be obvious to one of ordinary skill in the art.

Uses

The present invention may be used in various biological sciences. Genetic material may be delivered into selected cells for transformation. Cytotoxic material (e.g., encapsulated toxins and radioisotopes) may be delivered into selected cells for therapy. Markers (e.g., visible dyes, fluorescing compounds, radioisotopes) may be delivered into selected cells for diagnosis. Materials which permit the recovery of cells (e.g., iron) may be delivered into cells for recovery by physical techniques (e.g., density methods). Foreign bipolymers, such as RNA, protein, lipids and both organic and inorganic chemicals, may be inserted into cells and then analyzed.

Specific applications of the present invention include transformation of plant cells, animal cells, and microorganisms.

Plant Cell Transformation

An appealing feature of the present invention is that it allows treatment of plant cells whose walls are intact. Because the obstacle of regenerating whole plants from protoplasts may be circumvented, the genetic engineering of important grain species may be facilitated.

Two important targets for plant germline transformation are pollen or eggs, and meristem domes or tissue culture cells (from intact plants and embryos, or from tissue culture). Transformation of pollen, eggs, or meristem domes are possible methods for sexually-propagated crops, while transformation of tissue culture cells or meristematic domes are possible methods for asexually-propagated crops. Each of these approaches is capable of producing transformed whole plants.

Tissue culture cells may be transformed, and then cultured to provide somatic embryos or meristem domes, which in turn regenerate into transferred plants.

Meristem transformation, for example, may be achieved by surgically exposing the meristematic dome, and bombarding it with DNA-bearing particles, permitting a large number of meristematic cells to be transformed. The transformed meristems would be grown into chimeric shoots, from which stable transformed sectors are selected.

For a general discussion of a process wherein genes were inserted into immature embryo axes, which are then used to regenerate plants, see Stable Transformation of Soybean (Glycine max) by Particle Acceleration, 1998, D. E. McCabe, W. F. Swain, B. J. Martinell and P. Christon, *Bio/Technology*, Vol. 6, pp. 923-926.

Finally, chloroplast transformation in Chlamydomonas, a unicellular algae, using microprojectile bombardment has also been reported (J. E. Boynton, N. W. Gillham, E. H. Harris, J. P. Hosler, A. M. Johnson, A. R. Jones, B. L. Randolph-Anderson, D. Robertson, T. M. Klein, K. B. Shark and J. S. Sanford, 1988 *Sci.*, 240:1543-1537. Three mutants of the chloroplast atpB gene of the Chlamydomonas reinhardtii were transformed with chloroplast DNA containing the wild-type gene. Photosynthetic capacity was restored in the transformants.

Animal Cell Transformation

The genetic transformation of small groups of cells in animal tissues is now possible using the method and apparatus of the present invention. Such a therapy provides a non-infectious, but highly efficient, mechanism for the transformation of animal tissues, in situ. For a general discussion, see Delivery of Substances into Cells and Tissue, using a Particle Bombardment Process, J. C. Sanford, T. M. Klein, E. D. Wolf, and N. Allen, *Particular Scic. and Technol.*, 5:27-37.

Microorganism Transformation

The transformation of mitochondria in yeast by bombardment with projectiles has been reported (S. A. Johnston, P. Q. Anziano, K. Shark, J. S. Sanford and R. A. Butow, 1988, Mitochondrial Transformation in Yeast by Bombardment with Microprojectiles, *Sci.*, 240:1538-1541. A nonreverting strain of yeast which is respiratory deficient was transformed with DNA sequences that could correct the oxi 3 deletion.

Genetic material may also be shot into isolated subcellular organelles such as mitochondria or chloroplasts. The transformed organelles may then be reinserted into selected cells.

The following examples are presented to further illustrate but not limit the scope of this invention. All parts and percentages are by weight unless otherwise indicated.

EXAMPLES

The propellable matter is prepared as follows.

Carrier particles coated with DNA-containing plasmids are suspended in a carrier medium. More specifically, the plasmid is adsorbed to the surface of gold particles. The plasmid contains a gene which encodes for the enzyme beta-glucuronidase (GUS gene) and which is under the control of a 35s California Mosaic Virus (CaMV) promoter (gene, promoter and regulatory sequences obtained from Clontech Laboratories, Inc., Palo Alto, CA). The gold particles are spherical powder of about 1.5-3.0 microns in diameter (commercially available from Alfa Products, Danvers, MA).

To accomplish adsorption, 50 µl of a plasmid solution (1.8 µg of DNA per µl of 0.01 M Tris buffer, pH 8.0, with 0.001 M ethylene diamine tetraacetic acid (EDTA) is added to 400 µl of a suspension of gold carrier particles (300 mg of gold carrier particles per milliliter (ml) of distilled water). The DNA is precipitated by the addition of 74 µl of a 2.5 M calcium chloride solution and 30 µl of a 0.1 M spermidine solution. The coated carrier particles are allowed to settle to the bottom of an Eppendorf tube and the resultant clear liquid is completely drawn off. The carrier particles are resuspended in 500 µl ethanol (100%) (carrier medium). One carrier particle is coated with approximately 10 copies of the plasmid.

The target matter is prepared as follows. Suspension cultures of cultivar Black Mexican Sweet (BMS) pea cells are obtained from Professor Virginia Walbot (Stanford University). The BMS are described in W. F. Sheridan, 1975, *J. Cell. Biol.*, 67:3969. These cultures are routinely maintained in a liquid Murashige and Skoog (MS) medium (Physiol. Plantarum, 1962, 15:473-496) supplemented with 2,4-dichlorophenoxyacetic acid (2 mg/liter).

In preparation for bombardment with the carrier particles, a 100 mg sample of cells is collected from suspension on a 7 cm Whatman no. 1 filter paper by vacuum filtration on a Buchner funnel. The filter paper with the cells are placed in a 9 cm Petri dish which contains the MS medium, described above, in solid form.

The apparatus used to accelerate the coated gold particles at the BMS pea cells consists of the following elements, which were previously shown in FIGS. 1, 2, 3 and 4A:

(1). A 1A size gas cylinder (i.e., gas supply means 31) filled with helium gas is in fluid communication with a stainless steel capillary tube having dimensions of 7'×0.02"I.D. (i.e., gas supply line 33). The gas supply lines is in operative combination with a standard two-stage pressure regulating valve, commercially available from Victor Equipment Co. (i.e., gas regulating valve 32a). The gas supply line is in turn in communication with a high pressure stainless steel gas chamber having dimensions of ⅛"O.D.×3" length (i.e., gas reservoir 32b).

(2). A 3 cubic centimeter (cc) Luer Lok sterile syringe (i.e., propellable matter supply means 21a) is in fluid communication with 1/10" Teflon (trademark of E. I. DuPont de Nemours Co.) FEP tubing (i.e., propellable matter supply line 23). The tube is in operative combination with a Rheodyne Model 7030 3-way valve (i.e., multipurpose valve 70).

(3). A clear 1/10" OD FEP tube (i.e., recovery means, 60).

(4). A pyrex glass tube having dimensions of 10 cm×1.2 mm O.D.×0.8 I.D. mm (i.e., delivery means 50).

(5). A velocity detection means comprises two sensors adjacently positioned relative to each other on the delivery means 50. Each sensor (i.e., first sensor 92 and second sensor 94) comprises a photodiode and an infrared emitter. The photodiodes are commercially available from Motorola under the trade designation MRD5ϕϕ, and the infrared emitters are commercially available from General Electric under the trade designation LED55C.

The first and second sensors are in operative combination via an electric circuit having a design as shown in the schematic representation of FIG. 8. FIGS. 8A and 8B.

Provided below is a detailed explanation of FIGS. 8A and 8B, depicting the operative combination between the velocity detection means 90 and the multipurpose valve 70.

Block 113 provides sequence timing to ensure that after actuation means (i.e., firing button 113a) is pressed, all other parts of the circuit are prepared for the timing cycle. Block 113 sends signal 113b' simultaneously indirectly, via block 112 (received as signal 113b"), the flip flop 115a (received as signal 112b) to stop the timer, and signal 113b' directly to flip flop 115b (received as signal 113b") to reset block 115 to accept only one start signal (111b) and to clear the count timer block 116 to zero. The indirect signal is provided as a fail safe to stop the timer in case the optics of second sensor 94 does not register the passing of propellable material. Block 113 then provides signal 113c to begin the actuation of a timer in Block 114.

Block 114 accepts signal 113c from block 113 and then provides a preselected time interval, operating a 4-way valve (i.e., 114b on FIG. 8A) that sends a selected volume of air pressure to a pneumatic actuator (not shown) on the multipurpose valve 70, operating valve 70 to provide communication between the source of gas under pressure and the propellable matter reservoir.

Block 111 accepts signal 111a, generated by the propellable matter passing between the source means and sensor means of first velocity sensor 92 and conditions the signal, producing a sharp rising voltage signal corresponding in time to the decreasing voltage of signal 111a, i.e., a "start" signal 111b capable of starting a timer (block 116 in FIG. 8B).

Block 112 accepts signal 112a, generated by the propellable matter passing between combination of source means and sensor means of second velocity sensor 94, and produces a sharp rising voltage signal corresponding in time to the decreasing voltage of signal 112a, i.e. a "stop" signal 112b capable of stopping the timer (block 116 in FIG. 8B).

Flip flop 115a accepts the "start" signal 111b from block 111, the "stop" signal 112b from block 112 and flip flop 115b accepts the "clear timer" signal (113b") from the sequence block 113, and maintains the timing status, i.e., allowing only one timing cycle per delivery cycle of the propellable matter. Flip flop 115a generates signal 115c, which is sent to Block 116.

Block 116 comprises a quartz crystal stabilized timer comprising a clock integrated circuit 116a and a digital counter 116b. Block 117 comprises a display for displaying the time of flight of the most recent propellable matter.

Digital counter 116b accepts the timing status signals 113b" and 115c from block 115. These timing status signals are "timer run" (i.e., 115c) and "timer clear" (i.e., 113b"). When the timer run signal is approx. $\phi$ volts, the timer block counts micro-seconds up from zero. When the timer run signal is approx. 12 volts, the timer stops and holds the last count. When the timer clear signal is approximately $\phi$ volts, the timer can run. When the timer clear signal is approximately 12 volts, the timer is cleared to zero. The display block 117 accepts multiplexed binary coded decimal (BCD) numeric signals from block 116, and thus displays the most recent time of flight of the propelled material in microseconds on the front panel display.

Although an exemplary circuit has been shown, many circuits are possible to achieve the same result.

(6) A dual three-way valve (multipurpose valve 70), having two subvalves (subvalve 70a and 70b), commercially available from Rheodyne, Inc., Cotati, CA under the trade designation model 7030 ARV. The subvalves of the dual three-way valve 70 ares in operative combination with a pneumatic actuator, kit #41687 commercially available from Anspec Co., Ann Arbor, MI. The pneumatic actuator is driven by air supplied from a four-way solenoid valve, commercially available from the Automatic Switch Company (ASCO), Florham Park, NJ.

(7). An external loop 40 made of stainless steel 1/16" O.D. (i.e., propellable matter reservoir) is in operative combination with the first and second three-port valves.

The first three-port valve provides selective fluid communication between the propellable matter supply means or the gas reservoir, and the propellable matter reservoir.

The second three-port valve provides selective fluid communication between the propellable matter reservoir and the recovery means or the delivery means.

The multipurpose valve is initially set in order to provide fluid communication between the syringe and the propellable matter and to block pneumatic communication between the gas reservoir and the propellable matter reservoir.

The syringe which will deliver about 1 ml of the propellable matter (carrier medium suspension of coated particles), is placed in fluid communication with the propellable matter supply line. The propellable matter supply line is in fluid communication with the propellable matter reservoir.

The propellable matter regulating valve 22*a* is opened to provide fluid communication between the propellable matter supply means and the propellable matter reservoir. After a selected volume of propellable matter is emitted into the propellable material reservoir, the propellable matter valve is closed.

Any volume of propellable matter in excess to the volume of the propellable matter reservoir is released through the recovery means.

The gas regulating valve 32*a* is opened to provide pneumatic communication between the gas supply means and the gas reservoir. A gas pressure of about 1000 psi is obtained in the gas reservoir. The gas regulating valve is then closed.

The remainder of the operation is controlled via the circuit set forth in FIGS. 8A and 8B. The circuit operates as follows.

After the firing button 113*a* is pressed, block 113 provides a sequence timing of about 0.05 seconds to halt the digital timer of block 116. Block 115 holds the status of block 116, i.e., if by error the digital timer is still timing after a previous actuation of the apparatus, the digital timer is cleared to zero in preparation for the next timing cycle. After the digital timer is stopped, the timer status of block 115 is set to accept only one start signal from block 111.

Next, the interval timer block 114 is started. The interval timer block 114 supplies a preset time interval of 0.8 seconds of 120 volts alternating current (VAC) to actuate valve 114*b*, supplying about 65 to about 75 pounds per square gauge (psig) of air to drive a pneumatic actuator (not shown) on the multipurpose valve 70 to set the multipurpose valve to provide selective communication between the source of gas and the propellable matter reservoir, and resulting in the acceleration of the pressurized gas and propellable matter past the first and second sensors.

As the leading edge of the propellable matter passes the first sensor of the velocity detection means, an electrical signal (111*a*) is generated. When conditioned by block 111, the electric signal is the signal used by block 115 to start the digital timer block 116.

Similarly, as the leading edge of the propellable matter passes the second sensor of the velocity detection means, an electrical signal (112*a*) is generated. When conditioned by block 112, the electric signal is the signal used by block 115 to stop the digital timer block 116. The time of flight of the leading edge of the propellable matter between the first sensor means and the second sensor means is displayed on (the 3 digit, 7 segment, LED display of block 117 (117*b*) a multisegment LED indicator.

As seen in FIG. 9, lines 1 and 2 indicate the time of flight of the propellable matter past first sensor 92 and second sensor 94, respectively. The time of travel between the first and second sensors, which are separated by 2.8 centimeters, was 60 milliseconds. This indicates that the propellable matter is traveling at a velocity of about 1044 miles per hour.

The propellable matter exits from the delivery means toward the BMS cells in a propulsion zone. The propulsion zone is defined by a vacuumed chamber, the design of which is taught in "Fisher 88", supra, p. 114. The pressure in the propulsion zone is about 0.1 atm absolute.

The operation is completed by selectively setting the valve in order to block the passage of gas from the gas reservoir through the valve into the delivery means, and to provide fluid communication between the syringe and the propellable matter overflow reservoir.

Monolayers of BMS cells on Petri plates of MS medium are bombarded simultaneously. There are approximately 100 mg BMS cells on each petri dish. The carrier particles coated with the GUS-containing plasmid are delivered into the BMS cells.

Following bombardment of the BMS cells, the culture is incubated in the dark for about 2 days at 27° C. After two days, the cells are assayed for GUS activity.

Expression of the GUS gene in the BMS cells is observed by using the GUS histochemical assay (5-Br-4-Cl-3 indolyl-beta-D-glucuronic acid [$x$-gluc] substrate and procedure obtained from Clontech Laboratories. Inc., Palo Alto, CA). The BMS cells and cell clumps are incubated at 37° C. for 24 to 48 hours in solution of 1 millimolar (mM) $x$-gluc containing 0.5 mM potassium ferricyanide, 0.5 mM potassium ferrocyanide and 10 mM EDTA. The cells and cell clumps which turn blue with this assays are scored as positive for GUS activity.

The results are set forth in Table 1.

TABLE 1

| Bombardment Schedule | Number of BMS cells or cell clumps with GUS activity/petri dish |
|---|---|
| cells bombarded with gold particles coated with plasmid containing GUS gene | 4 |
| cells bombarded with gold particles coated with plasmid containing GUS gene | 5 |
| cells bombarded with gold particles coated with plasmid containing GUS gene | 6 |
| cells bombarded with gold particles coated with plasmid containing GUS gene | 4 |
| cells bombarded with gold particles coated with plasmid containing GUS gene | 5 |
| cells bombarded with gold particles coated with plasmid containing GUS gene | 2 |
| cells bombarded with gold particles coated with plasmid containing GUS gene | 10 |
| cells bombarded with gold particles coated with plasmid containing GUS gene | 8 |
| cells bombarded with gold particles coated with plasmid containing GUS gene | 9 |

These findings indicate that particle bombardment can be used to deliver DNA into intact plant cells simultaneously and that the gene introduced by this process can subsequently be expressed.

As is apparent from the foregoing specification, various modifications of the invention in addition to those shown and described herein will become apparent to those skilled in the art from the foregoing description and accompanying drawings. For this reason, it is to be fully understood that all of the foregoing is intended to be merely illustrative and is not to be construed or interpreted as being restrictive or otherwise limiting of the present invention, excepting as it is set forth and defined in the hereto-appended claims.

What is claimed is:

1. An apparatus comprising the following:
    (a) a source of gas under pressure having a gas outlet and a source of propellable matter having an outlet;
    (b) a propellable matter reservoir having an inlet and an outlet;
    (c) a delivery means having an inlet and an outlet, wherein the inlet of the delivery means is in communication with the outlet of the propellable matter reservoir, and
    (d) a multipurpose valve means for providing selective pneumatic communication between either the outlet of the source of gas under pressure or the outlet of the source of propellable matter, and the inlet of the propellable matter reservoir, and for providing selective communication between the inlet of the delivery means and the outlet of the propellable matter reservoir, the source of gas under pressure, when in communication with the propellable matter reservoir, gas is discharged into the propellable matter reservoir, and said gas being under sufficient pressure to cause a propellable matter to exit the delivery means, when the propellable matter reservoir is in communication with the delivery means, at a velocity of between about 200 miles per hour (mph) to about 1200 mph.

2. The apparatus of claim 1, wherein the apparatus further comprises
    (e) a recovery means having an inlet, and
    the multipurpose valve means provides for selective pneumatic communication between either the outlet of the source of gas under pressure or the outlet of the source of propellable matter, and the inlet of the propellable matter reservoir, and further provides for selective communication between the inlet of the recovery means and the outlet of the propellable matter reservoir.

3. The apparatus of claim 1, wherein the delivery means comprises a sighting means.

4. The apparatus of claim 1, wherein the source of gas under pressure comprises
    (1) a gas supply means having an outlet, and
    (2) a gas regulating means, said gas regulating means being in operative combination with the gas supply means to provide selective communication between the gas supply means outlet and the inlet of the propellable matter reservoir.

5. The apparatus of claim 4, wherein the gas regulating means comprises a gas valve and a gas reservoir having an inlet, wherein the gas valve provides selective pneumatic communication between the gas supply means outlet and the gas reservoir inlet.

6. The apparatus of claim 1, further comprising a temperature regulating means, said temperature regulating means being in operative combination with the propellable matter reservoir.

7. The apparatus of claim 1, wherein the source of propellable matter comprises
    (1) a propellable matter supply means having an outlet, and
    (2) a propellable matter regulating means, said propellable matter regulating means being in operative combination with the propellable matter supply means to provide selective communication between the propellable matter supply means outlet and the inlet of the propellable matter reservoir.

8. The apparatus of claim 7, wherein the source of propellable matter further comprises an agitation means, said agitation means being in operative combination with the propellable matter supply means.

9. The apparatus of claim 3, wherein the delivery means comprises a macroaiming means.

10. The apparatus of claim 3, wherein the delivery means comprises a microaiming means.

11. The apparatus of claim 3, wherein the apparatus comprises a velocity detection means.

12. The apparatus of claim 11, wherein the apparatus comprises a first sensor and a second sensor.

13. The apparatus of claim 1, wherein the propellable matter reservoir is in fluid communication with an environmentally-controlled chamber, said chamber defining a propulsion zone.

14. An apparatus comprising the following:
(a) a source of gas under pressure having a gas outlet and a source of propellable matter having an outlet;
(b) a propellable matter reservoir having an inlet and an outlet;
(c) a delivery means having an inlet and an outlet, wherein the inlet of the delivery means is in communication with the outlet of the propellable matter reservoir, and
(d) a multipurpose valve means for providing selective pneumatic communication between either the outlet of the source of gas under pressure or the outlet of the source of propellable matter, and the inlet of the propellable matter reservoir, and for providing selective communication between the inlet of the delivery means and the outlet of the propellable matter reservoir, the source of gas under pressure, when in communication with the propellable matter reservoir, gas is discharged into the propellable matter reservoir and said gas being under sufficient pressure to cause a propellable matter to exit the delivery means, when the propellable matter reservoir is in communication with the delivery means, at a velocity of effective to cause a noncellular biological material to enter a biological cell.

* * * * *

UNITED STATES PATENT AND TRADEMARK OFFICE
CERTIFICATE OF CORRECTION

PATENT NO. : 5,141,131

DATED : August 25, 1992

INVENTOR(S) : Theodore E. Miller, Jr.; Bradley C. Schuchardt, Alan R. Gould, Thomas A. Skokut It is certified that error appears in the above-identified patent and that said Letters Patent is hereby corrected as shown below:

Column 24, line 66, "milliseconds" should read -- microseconds --.

Figure 9:
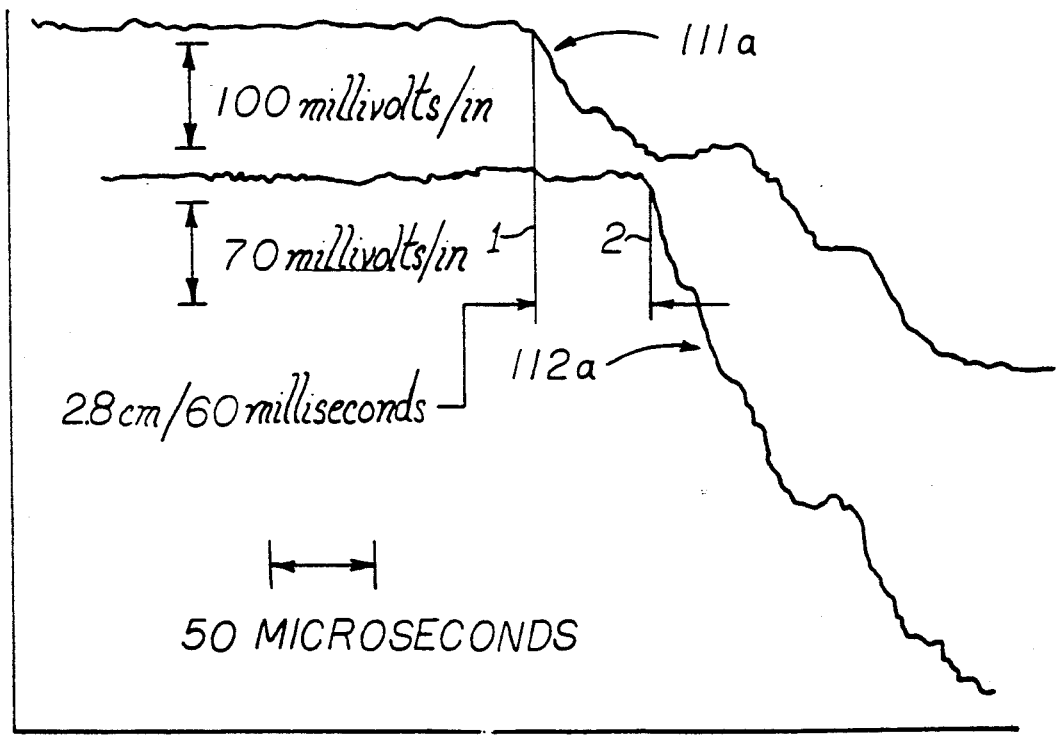

In Figure 9, "milliseconds" should read -- microseconds --.

Signed and Sealed this

Thirtieth Day of November, 1993

Attest:

BRUCE LEHMAN

Attesting Officer

Commissioner of Patents and Trademarks